US009248421B2

(12) United States Patent
Lee et al.

(10) Patent No.: US 9,248,421 B2
(45) Date of Patent: Feb. 2, 2016

(54) PARALLEL INTEGRATED BIOREACTOR DEVICE AND METHOD

(75) Inventors: Harry Lee, Malden, MA (US); Rajeev Ram, Arlington, MA (US); Klavs Jensen, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1637 days.

(21) Appl. No.: 11/545,647

(22) Filed: Oct. 10, 2006

(65) Prior Publication Data

US 2008/0299539 A1   Dec. 4, 2008

Related U.S. Application Data

(60) Provisional application No. 60/724,971, filed on Oct. 7, 2005, provisional application No. 60/780,982, filed on Mar. 10, 2006.

(51) Int. Cl.
*C12M 3/00* (2006.01)
*B01F 11/00* (2006.01)
*B01F 13/00* (2006.01)
(Continued)

(52) U.S. Cl.
CPC ......... *B01F 11/0045* (2013.01); *B01F 13/0059* (2013.01); *B01L 3/5027* (2013.01); *C12M 23/16* (2013.01); *C12M 23/22* (2013.01); *C12M 23/44* (2013.01); *C12M 29/14* (2013.01); *C12M 29/26* (2013.01); *C12M 33/07* (2013.01); *C12M 41/26* (2013.01); *C12M 41/34* (2013.01); *C12M 41/40* (2013.01); *B01F 2215/0431* (2013.01); *B01F 2215/0454* (2013.01); *B01L 3/5025* (2013.01); *B01L 3/50273* (2013.01); *B01L 3/502738* (2013.01); *B01L 7/00* (2013.01); *B01L 2300/0867* (2013.01); *B01L 2300/10* (2013.01);
(Continued)

(58) Field of Classification Search
CPC ...... C12M 23/16; C12M 23/40; C12M 23/44; C12M 27/00; C12M 27/02; C12M 29/14; C12M 33/07; B01F 11/0045; B01F 13/0059; B01L 3/50273; B01L 3/502738; B01L 2400/0487
See application file for complete search history.

(56) References Cited

U.S. PATENT DOCUMENTS

2004/0077075 A1   4/2004   Jensen et al.
2005/0089993 A1   4/2005   Boccazzi et al.
(Continued)

FOREIGN PATENT DOCUMENTS

WO   WO 01/68257    9/2001
WO   WO 03/093406   11/2003

OTHER PUBLICATIONS

International Search Report for PCT/US2006/039475, mailed Apr. 19, 2007.
(Continued)

*Primary Examiner* — William H Beisner
(74) *Attorney, Agent, or Firm* — Wolf, Greenfield & Sacks, P.C.

(57) ABSTRACT

In one embodiment, the present invention introduces integrated fluid injection and mixing devices to enable pH control in a miniature parallel integrated bioreactor array system. In another embodiment, the environmental conditions of the growth chamber is enabled through fluidic injections in a miniature parallel cell culture system. In still another embodiment, the present invention utilizes gas switches to control oxygen concentration within a miniature parallel integrated bioreactor array.

57 Claims, 17 Drawing Sheets

(51) Int. Cl.
*C12M 3/06* (2006.01)
*C12M 1/26* (2006.01)
*C12M 1/34* (2006.01)
C12M 1/06 (2006.01)
C12M 1/00 (2006.01)
B01L 3/00 (2006.01)
B01L 7/00 (2006.01)

(52) U.S. Cl.
CPC ......... *B01L 2400/0487* (2013.01); *C12M 23/40* (2013.01); *C12M 27/02* (2013.01)

(56) References Cited

U.S. PATENT DOCUMENTS

2005/0106045 A1 5/2005 Lee
2006/0199260 A1 9/2006 Zhang et al.
2009/0220935 A1 9/2009 Lee et al.

OTHER PUBLICATIONS

Written Opinion for PCT/US2006/039475, mailed Apr. 7, 2008.
International Preliminary Report on Patentability Chapter I for PCT/US2006/039475, mailed Apr. 9, 2008.
D. Weuster-Botz, *Adv. Biochem Eng. Biotechnol.*, 2005, 92, 125-143.
W. A. Duetz, L. Ruedi, R. Hermann, K. O'Connor, J. Buchs and B. Witholt, *Appl. Environ. Microbiol.*, 2000, 66, 2641-2646.
D. Weuster-Botz, J. Altenbach-Rehm and M. Arnold, *Biochem. Eng. J.*, 2001, 7, 163-170.
J. Altenbach-Rehm, C. Nell, M. Arnold and D. Weuster-Botz, *Chem. Eng. Technol.*, 1999, 22, 1051-1058.
S. R. Lamping, H. Zhang, B. Allen and P. Ayazi Shamlou, *Chem. Eng. Sci.*, 2003, 58, 747-758.
Y. Kostov, P. Harms, L. Randers-Eichhorn and G. P. Rao, *Biotechnol. Bioeng.*, 2001, 72, 346-352.
P. Harms, Y. Kostov, J. A. French, M. Soliman, M. Anjanappa, A. Ram and G. Rao, *Biotechnol. Bioeng.*, 2006, 93, 6-13.
R. Puskeiler, A. Kusterer, G. T. John and D. Weuster-Botz, *Biotechnol. Appl. Biochem.*, 2005, 42, 227-235.
R. Puskeiler, K. Kaufmann and D. Weuster-Bostz, *Biotechnol. Bioeng.*, 2005, 89, 512-523.
D. Weuster-Botz, R. Puskeiler, A. Kusterer, K. Kaufmann, G. T. John and M. Arnold, *Bioprocess Biosyst. Eng.*, 2005, 28, 109-119.
M.M. Maharbitz, W. J. Holtz, R. T. Howe and J. D. Keasling, *Biotechnol. Bioeng.*, May 20, 2004; 86, 485-90.
F. K. Balagadde, L. You, C. L. Hansen, F. H. Arnold and S. R. Quake, *Science.*, 2005, 309, 137-40.
A. Zanzotto, N. Szita, P. Boccazzi, P. Lessard, A. J. Sinskey and K. F. Jensen, *Biotechnol. Bioeng.*, 2004, 87, 243-254.
P. Boccazzi, A. Zanzotto, N. Szita, S. Bhattacharya, K. F. Jensen and A. J. Sinskey, *Appl. Microbiol. Biotechnol.*, 2005, 68, 518-532.
Z. Zhang, N. Szita, P. Boccazzi, A. J. Sinskey and K. F. Jensen, *Proceedings of Micro Total Analysis Systems, Seventh International Conference on Miniaturized Chemical and Biochemical Analysis Systems*, Squaw Valley, California, USA, 2003, The Transducer Research Foundation, San Diego, California, Oct. 2003, pp. 765-768.
N. Szita, P. Boccazzi, Z. Zhang, P. Boyle, A. J. Sinskey and K. F. Jensen, *Lab Chip*, 2005, 5, 819-826.

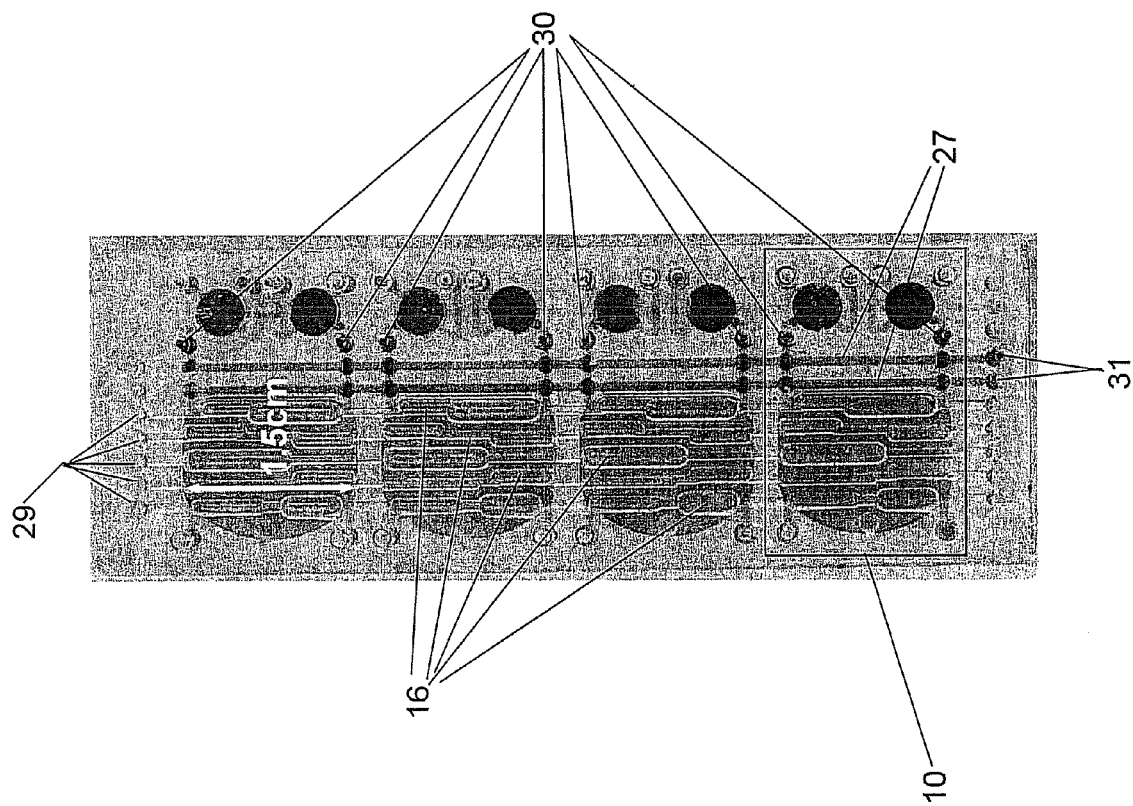

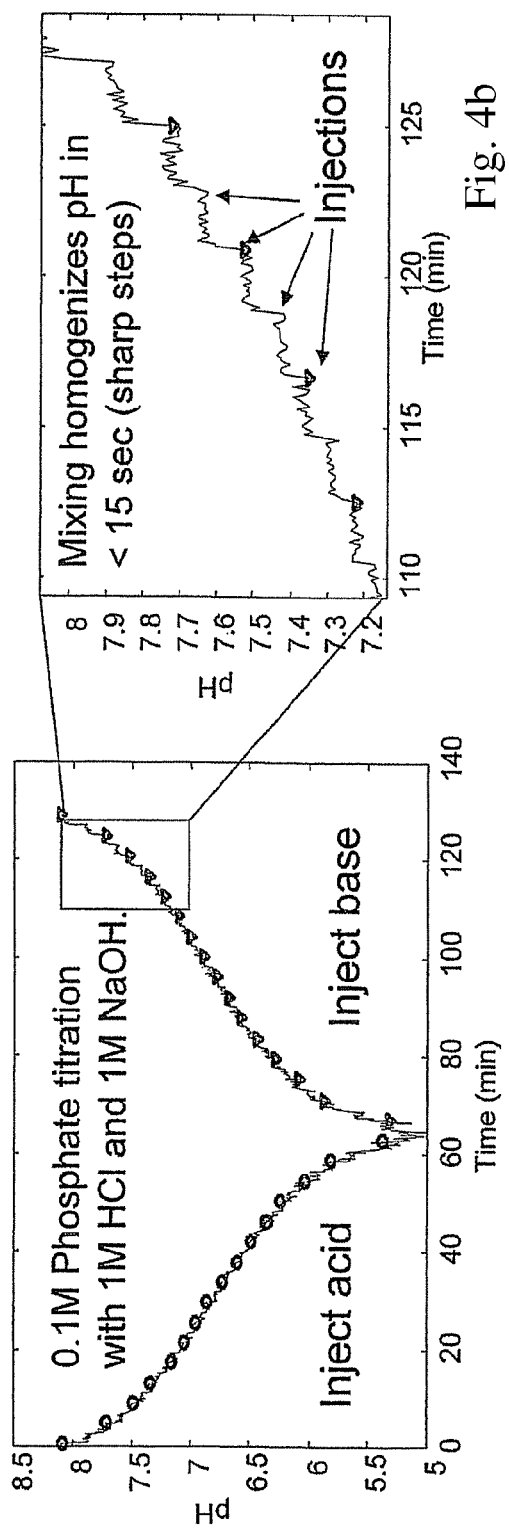
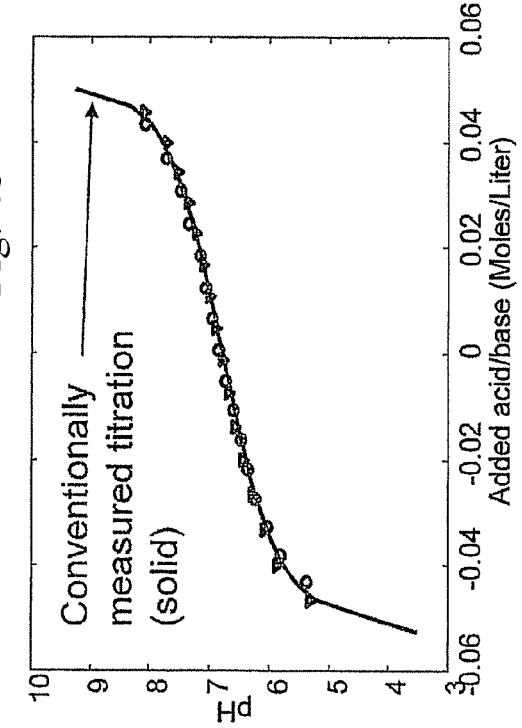
Fig. 4a
Fig. 4b
Fig. 4c

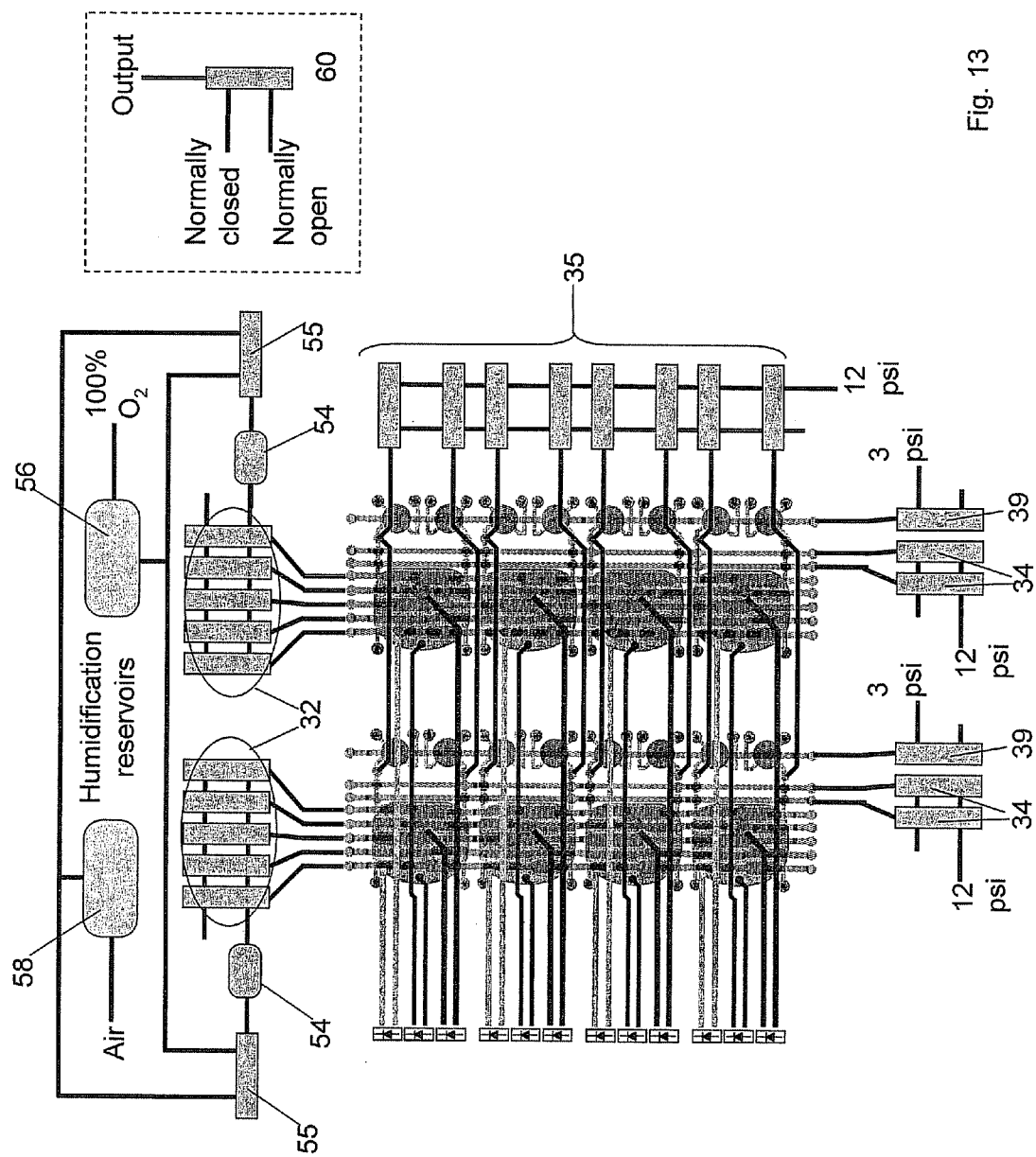

PARALLEL INTEGRATED BIOREACTOR DEVICE AND METHOD

PRIORITY INFORMATION

This application claims priority under 35 U.S.C. §119(e) to U.S. Provisional Patent Application Ser. No. 60/780,982, filed Mar. 10, 2006, and entitled "Method for Dissolved Oxygen Control in Parallel Integrated Bioreactor Array," and U.S. Provisional Patent Application Ser. No. 60/724,971, filed Oct. 7, 2005, and entitled "Parallel Integrated Bioreactor Array," each of which is incorporated herein by reference in its entirety for all purposes.

BACKGROUND OF THE INVENTION

A critical driving force behind research in bioprocess science and engineering continues to be the demand for fast and accurate analytical information that can be used, for example, to evaluate the interactions between biological systems and bioprocess operations. One significant challenge is to carry out large numbers of experiments rapidly and effectively. This issue is of particular importance since many of the advances in molecular biology now lead to large numbers of potential biological systems that contain evolved biocatalysts, new pathway designs, and a variety of unique biological organisms from diverse sources.

Developing efficient and practical bioprocesses frequently involves testing a large number of different strains and environmental conditions in various combinations. Although the ultimate goal is to identify an appropriate strain and conditions for production on an industrial scale (e.g., in a bioreactor with a 1,000-300,000 liter volume), bioprocess development begins on a much smaller scale. For example, screening of different strains is often conducted in microtiter plates, under relatively uncontrolled conditions and with only limited possibility of monitoring conditions during culture. After identification of strains that appear promising, further screening is performed in shaking flasks with a much larger volume (e.g., 25-100 ml). Such flasks typically allow only partial control over important environmental variables and cannot achieve the high oxygen ($O_2$) concentrations typically used in large-scale fermentation processes. Thus the usefulness of these open loop systems for selecting the organism that will be optimal under actual bioprocess conditions is limited.

Scale-up to bench-scale, closed loop bioreactors, which offer improved control over environmental variables, increased oxygenation, and therefore the ability to achieve higher cell densities, is the next step. However, bench-scale reactors, with typical volumes of between 0.5 and 10 liters suffer from a number of drawbacks. Because of their large size, relatively high cost, and the time and effort required to obtain the data it is typically not practical to test as many combinations of strains and environmental conditions as would be desirable.

The inventors have recognized that there is a large technology gap between microtiter plates/flasks and closed loop controlled bioreactors. The gap is significant because its presence may allow potentially productive strains to be eliminated at the microtiter plate or shake-flask screening stage, due to optimization with respect to uncontrolled physical parameters, or it may allow potentially non-productive strains that do not perform well under typical industrial scale bioprocess conditions, e.g., high cell densities, to proceed to the next stage. There is thus a need in the art for a system to fill this gap. In particular, there is a need for small scale bioreactor systems that allow multiple experiments to be performed in parallel without an accompanying increase in cost, and that offer improved oxygen transfer capacity and control over environmental parameters, such as pH and dissolved oxygen.

Recent efforts to address the need for a parallel bioreactor system with the capabilities of a stirred tank reactor have focused on improving the oxygen transfer rate of microtiter plates (W. A. Duetz, L. Ruedi, R. Hermann, K. O'Connor, J. Buchs, and B. Witholt, Appl. Environ. Microb, 2000, 66, 2641-2646), improving the control capabilities of shake flasks (D. Weuster-Botz, J. Altenbach-Rehm, M. Arnold, Biochem. Eng. J, 2001, 7, 163-170), improving the parallelism of stirred tank bioreactors (J. Altenbach-Rehm, C. Nell, M. Arnold, and D. Weuster-Botz, Chem. Eng. Technol, 1999, 22, 1051-1058; S. R. Lamping, H. Zhang, B. Allen, P. Ayazi Shamlou, Chem. Eng. Sci., 2003, 58, 747-758; Y. Kostov, P. Harms, L. Randers-Eichhorn and G. P. Rao, Biotechnol Bioeng, 2001, 72, 346-352; P. Harms, Y. Kostov, J. A. French, M. Soliman, M. Anjanappa, A. Ram, and G. Rao, Biotechnol. Bioeng., 2006, 93, 6-13; R. Puskeiler, A. Kusterer, G. T. John and D. Weuster-Botz, Biotechnol. Appl. Biochem., 2005, 42, 227-235; R. Puskeiler, K. Kaufmann, D. Weuster-Botz, Biotechnol. Bioeng., 2005, 89, 512-523; D. Weuster-Botz, R. Puskeiler, A. Kusterer, K. Kaufmann, G. T. John, and M. Arnold, Bioprocess Biosyst Eng, 2005, 28, 109-119), or developing microfabricated bioreactor systems (M. M. Maharbiz, W. J. Holtz, R. T. Howe, and J. D. Keasling, Biotechnol. Bioeng., 2004,85, 376-381; F. K. Balagadde, L You, C. L. Hansen, F. H. Arnold, and S. R. Quake, Science. 2005, 309, 137-40; A. Zanzotto, N. Szita, P. Boccazzi, P. Lessard, A. J. Sinskey, and K. F. Jensen, Biotechnol. Bioeng., 2004, 87, 243-254; P. Boccazzi, A. Zanzotto, N. Szita, S. Bhattacharya, K. F. Jensen, A. J. Sinskey, Appl. Microbiol. Biotechnol, 2005, 68, 518-532; Z. Zhang, N. Szita, P. Boccazzi, A. J. Sinskey and K. F. Jensen, Proceedings of Micro Total Analysis Systems, Seventh International Conference on Miniaturized Chemical and Biochemical Analysis Systems, 765-768, Squaw Valley, Calif., USA, 2003; N. Szita, P. Boccazzi, Z. Zhang, P. Boyle, A. J. Sinskey and K. F. Jensen, Lab Chip, 2005, 5, 819-826). Each of these approaches has addressed parallelism, oxygenation, control, automation, and scalability to various degrees. Of these approaches, the miniature arrays of stirred tanks with robotic fluid handling have achieved the highest level of performance in terms of cell density and controlled parameters. However, these systems require expensive pipetting robotics and careful sterilization of the pipette tips to prevent contamination during frequent sampling.

The inventors have recognized that a microfabricated integration approach offers the potential for circumventing the need for robotic multiplexing, however, none of the microbioreactor systems developed to date have utilized microfluidic integration to achieve parallelism. In addition, no existing microfabricated approach has succeeded, even in a single reactor, in providing the oxygen transfer rate and the pH control capabilities of stirred tank bioreactors that are required for high cell density growth.

Current methods for pH control in miniature bioreactor arrays include diffusion of carbon dioxide gas into the liquid medium to generate carbonic acid, see, e.g., "Methods for intense aeration, growth storage, and replication of bacterial strains in microtiter plates," W. A. Duetz, L. Ruedi, R. Hermann, K. O'Connor, J. Buchs, and B. Witholt, Appl. Environ. Microb. Vol. 66, pp. 2641-2646 (June 2000) and "A microfluidic pH-regulation system based on printed circuit board technology," C. Laritz, and L. Pagel, Sensors and Actuators A, 84, 230 (2000), and generation of hydroxide or hydrogen ions by electrolysis of water, see, e.g., "A flow-through cell with integrated coulometric pH actuator," S. Bohm, W. Olthuis, and P. Bergveld, Sensors and Actuators B, 47, 48 (1998) and "Micro-instruments for life science research," B. van der Schoot, M. Boillat, and N. de Rooij, IEEE Transactions on Instrumentation and Measurement, 50, 1538 (2001). Carbon dioxide diffusion is limited because it cannot compensate for acids generated during microbial growth. While electrolytic methods can compensate for both acids and bases, unintended side reactions can generate unwanted compounds, and their implementation is complicated by the need to integrate a counter electrode with each growth chamber.

Furthermore, because diffusion of acids and bases to enable pH control is often slow at microbioreactor dimensions, controlling pH by simply injecting acid or base is not viable without something to facilitate mixing. Therefore, in order to realize a small scale bioreactor device that allows multiple experiments to be performed in parallel that offers improved oxygen transfer capacity and control over environmental parameters (such as pH and dissolved oxygen), a number of challenges need to be overcome.

SUMMARY OF THE INVENTION

The present invention addresses the need for a scalable, easy to use, bioreactor system capable of performing multiple bacteria or cell growth experiments under controlled conditions, and to high cell densities, among other things. In various embodiments, the method and apparatus of the present invention introduces integrated fluid injection and mixing devices to enable dissolved oxygen and/or pH control in a miniature parallel integrated bioreactor device, and is constructed using a simple molding process. In one embodiment, the device comprises a plurality of bioreactors (i.e., a bioreactor array), providing a system to allow a biologist or bioprocess engineer to optimize conditions for microbial growth, or for screening for the best performing strain under conditions approximating those of a full scale industrial process (e.g., high cell density, high oxygen transfer rate, control over pH, dissolved oxygen and temperature).

The ability to control pH and dissolved oxygen and provide a high oxygen transfer rate is important to distinguishing miniature bioreactor array systems from conventional microtiter plate cell culture. In contrast to the methods of the prior art, the fluid injection and mixing devices of the present invention can inject a fluid (e.g., containing acid, base, nutrients, test compounds, etc.) into a miniature cell culture system, enabling environmental control by altering environmental conditions. In further embodiments, the present invention comprises at least one gas switch for controlling the dissolved oxygen concentration in the miniature bioreactor. In various aspects, the device provides feedback control of the growth chamber environment, wherein the device may detect an environmental variable within the chamber and implement an appropriate response to maintain or change the conditions in the device. Implementation of an appropriate response may occur according to a predetermined scheme selected prior to the beginning of the bioreactor run, or a scheme adjusted during the bioreactor run either automatically or manually, and dependent upon the feedback from the bioreactor.

In one embodiment, the present invention is a parallel integrated bioreactor device comprising at least one growth chamber, at least one reservoir in fluidic communication with the growth chamber, at least one metered fluid injector to pass metered amounts of fluid from the reservoir into the growth chamber; and at least one sensor located within the growth chamber, wherein the sensor measures the pH properties of the growth chamber. In another embodiment, the present invention is a method of controlling the environmental conditions of a bioreactor comprising providing fluid injection to the growth chamber of the bioreactor to enable pH control in the growth chamber. In still another embodiment, the dissolved oxygen in the PIB device may be controlled by changing the oxygen concentration in the actuation gas. For example, the PIB may further comprise a gas mixing reservoir with a source of oxygen enriched air and a source of oxygen neutral or deficient air, and a gas switch for controlling oxygenation.

In a further embodiment, the plurality of bioreactors is arranged such that the macroscopic actuation resources, such as pneumatic pressure switches, and macroscopic sensor electronics and optoelectronics, such as photodetectors, amplifiers, and light emitting diodes, are shared such that the number of required macroscopic actuation resources does not scale linearly with the number of bioreactors and the number of macroscopic sensor electronic and optoelectronic components is less than the number of bioreactors.

The contents of all scientific articles, books, patents, and other publications, mentioned in this application are incorporated herein by reference. In addition, the following publications are incorporated by reference: Stephanopolous, G., ed. *Bioprocessing*. Second ed. *Biotechnology*, H.-J. Rehm, et al. (eds) Vol. 3. 1993, VCH Publishers Inc.: New York; Bailey, J. E. and D. F. Ollis, *Biochemical Engineering Fundamentals*. Second ed. McGraw-Hill chemical engineering series. 1986: McGraw-Hill, Inc.; Mulder, M., *Basic Principles of Membrane Technology*. Second ed. 1996: Kluwer Academic Publishers. In the event of a conflict or inconsistency between any of the incorporated references and the instant specification, the specification shall control, it being understood that the determination of whether a conflict or inconsistency exists is within the discretion of the inventors and can be made at any time.

BRIEF DESCRIPTION OF THE DRAWING

FIG. 1 is a photograph of one embodiment of the present invention, wherein the pressure chamber is shared between multiple bioreactors;

FIG. 4a is a plot showing pH versus time for titrations of 85 µL of 100 mM phosphate using one embodiment of the present invention, and 1 M of HCl/NaOH, wherein the markers indicate every other injection;

FIG. 4b is a enlarged view of a portion of the FIG. 4a graph, showing a pH resolution of 0.06;

FIG. 4c is plot of pH versus added acid/base aligned with a conventionally measured titration curve of the embodiment of FIG. 4a;

FIG. 13 illustrates connections for pneumatic actuation lines and optical fiber bundles according to another embodiment (a legend for the solenoid switch ports is shown in the box), wherein the first fluid injector valve is individually controlled across modules, and the next two injector valves are shared along a module;

DETAILED DESCRIPTION OF CERTAIN PREFERRED EMBODIMENTS OF THE INVENTION

I. Definitions

Figure 2A:
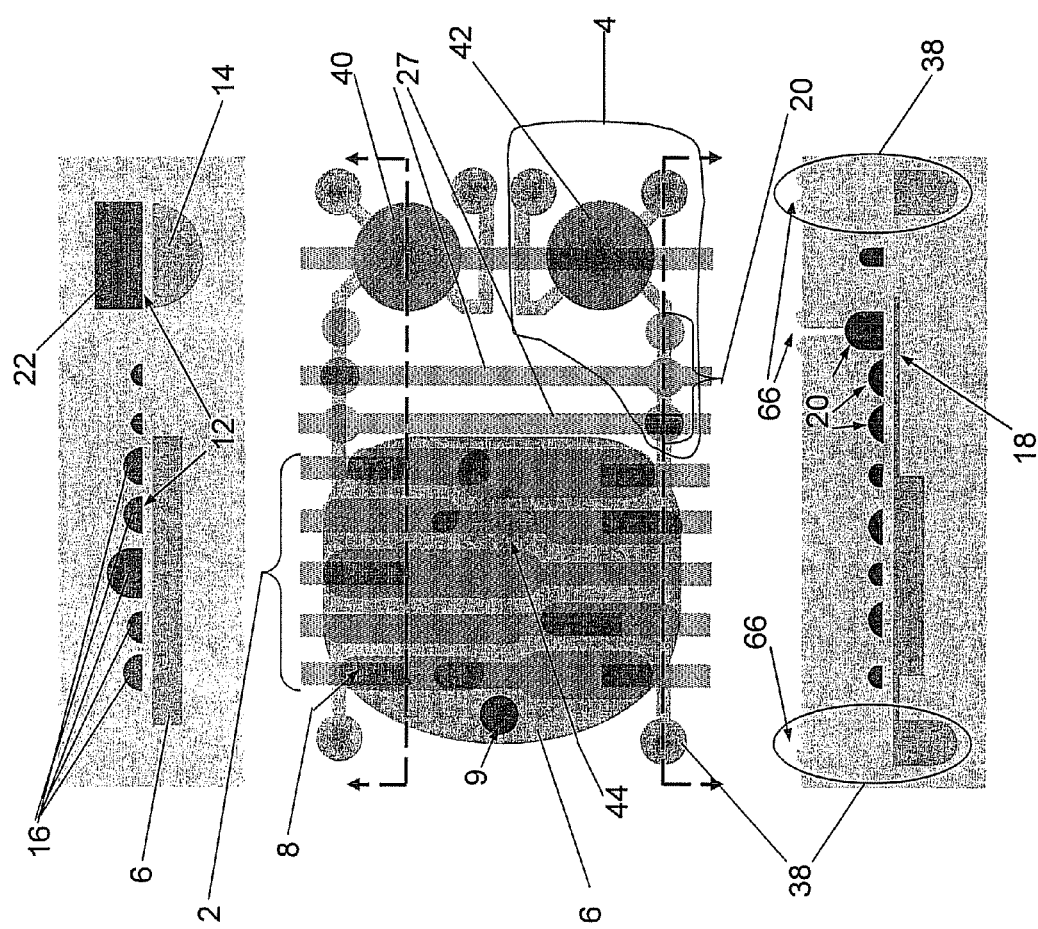
FIG. 2a shows a schematic cross-section of the integrated devices according to various embodiments of the present invention.

The following definitions are of use in understanding the invention.

Acid: As used herein, the term "acid" means any of various typically water-soluble compounds that in solution are capable of reacting with a base to form a salt, and have a pH less than 7, that are hydrogen-containing molecules or ions able to give up a proton to a base, or that are substances able to accept an unshared pair of electrons from a base.

Actuating lines or actuator: An "actuating line" or "actuator" refers to a device that puts another device or element of a system into action or motion.

Approximately. As used herein, the term "approximately" means that the measurement or number may deviate by 10% from the numeral given.

Base: As used herein, the term "base" refers to any of various typically water-soluble compounds that in solution have a pH greater than 7, are capable of reacting with an acid to form a salt, and are molecules or ions able to take up a proton from an acid or able to give up an unshared pair of electrons to an acid.

Channel: The term "channel" refers to a hole of constant or systematically varied cross-sectional area through a material. Generally a channel has a defined cross-sectional geometry, which may be rectangular, ovoid, circular, or one of those geometries with an imposed finer feature, such as indentations, etc.

Integrated: As used herein, the term "integrated" refers to being inseparable, or fabricated together.

Medium: As used herein, the term "medium" refers to a nutrient mixture that microbes are grown in.

Microchannel: As used herein, the term "microchannel" refers to a channel, i.e., a hole of consistent or systematically varied cross-section area through a material, having at least one dimension that may most conveniently be expressed in terms of micrometers. For example, the term "microchannel" may refer to a channel having at least one dimension of approximately 500 µm or less, approximately 100 µm or less, approximately 50 µm or less, approximately 20-50 µm, approximately 10-20 µm, approximately 5-10 µm, approximately 1-5 µm, approximately 1 µm, or between 0.1 and 1 µm. One of ordinary skill in the art will recognize that the dimensions of such channels may run into the millimeters, but that most dimensions are in the micrometer range.

Microreactor: As used herein, the term "microreactor" refers to a reactor, i.e., a device that contains a space in which a chemical or biochemical process (e.g., the growth of cells) is conducted, having an interior volume of less than 1 ml. Microreactors include microscale bioreactors, also referred to as microbioreactors.

Microscale. As used herein, "microscale" generally refers to structures having at least one dimension that may most conveniently be expressed in terms of micrometers. For example, the term "microscale structure" may refer to a structure having dimensions of approximately 500 µm or less, approximately 100 µm or less, approximately 50 µm or less, approximately 20-50 µm, approximately 10-20 µm, approximately 5-10 µm, approximately 1-5 µm, approximately 1 µm, or between 0.1 and 1 µm. One of ordinary skill in the art will recognize that the length of such structures may run into the millimeters, but that most dimensions are in the micrometer range.

Microscale bioreactor: As used herein, the term "microscale bioreactor" or "microbioreactor" is used to describe a bioreactor (i.e., an apparatus for culturing cells) having an interior volume of less than 1 ml. The terms "microscale bioreactor" and "microfermentor" are used interchangeably herein.

Miniature: As used herein, the term "miniature" generally refers to having dimensions substantially smaller than conventionally practiced in the art. "Miniature" may refer to structures having at least one dimension that may most conveniently be expressed in terms of millimeters. For example, "miniature bioreactor" may refer to a structure having a volume of approximately 10 mL or less, approximately, 7 mL or less, approximately between 5-7 mL, approximately 1-5 mL, or approximately less than 1 mL.

Parallel: Reaction runs, including but not limited to, fermentor runs are performed "in parallel" when the run times of the runs overlap. The runs may, but need not be, started and/or terminated at substantially the same time. The runs may last for the same length of time or for different lengths of time.

II. Overview

The present invention encompasses the recognition that microscale bioreactors (microfermenters) offer a means of addressing the continuing demand in bioprocess science and engineering for fast and accurate analytical information that can be used to evaluate the interactions between biological systems and bioprocess operations. In addition, such systems provide a platform for efficiently incorporating modern tools of biology (e.g., genetics, enzymology, molecular biology, and bioinformatics) to improve bioprocess screening and development. For example, microscale bioreactors allow the rapid screening of strains and metabolic pathways for applications ranging from synthesis of natural products to bioremediation. Bioprocess technology has been instrumental in the development of large-scale production of numerous pharmaceuticals and vaccines. In addition, bioprocesses are employed in the food industry, waste treatment, etc.

Metabolic pathway engineering is making a profound impact in areas as diverse as drug discovery (e.g., through the synthesis of novel natural products, commodity chemicals and the biodegradation of toxic pollutants). Metabolic engineering encompasses the targeted improvement of products formation or cell properties through the modification of biochemical reactions. Hence, metabolic engineering focuses on determining the enzymes that offer the greatest amount of control over the rate of production of a certain metabolite (metabolic control analysis or "MCA"), then altering the activity of those enzymes (e.g., via molecular biology) and/or altering relevant reaction conditions to manipulate product yields. MCA can involve making mathematical models, carbon tracing, and developing assays for obscure metabolites and acids in the understanding of metabolic fluxes. The alteration of enzyme activities can involve genetic library construction, screening, cloning, and other molecular biology tools. Microfermenter technology will have a significant impact both on how bioprocess development and metabolic engineering research are carried out and also on how rapidly research can be translated into improvements in bioprocess.

The parallel integrated bioreactor ("PIB") device of the present invention facilitates bioprocess development by bridging the technological gap between relatively uncontrolled systems (e.g., shake flasks, microtiter dishes, etc.), which can be inexpensively operated in parallel, and bench scale bioreactor experiments, which provide more control but are much more inconvenient to operate in parallel. In this aspect, the PIB device enables the growth of microorganisms in multiple feedback-controlled environments in parallel. In various embodiments, the PIB of the present invention has few moving parts, and simple setup and operation. The system may be fully automated, including automated data acquisition; the system therefore may require no user intervention. Furthermore, in various aspects, the device of the present invention could fit into a small footprint, with dimensions in the height and width ranges of approximately 1-25 inches. Table 1 sets forth exemplary characteristics of standard bioprocess development tools and highlights the performance bridge provided by various aspects of the present invention. As shown by the Table, the various aspects of the present invention may provide a factor of five (5) step in oxygen transport to bridge the factor of ten (10) jump between shake flasks and bioreactors. Furthermore, the various aspects of the present invention may provide closed loop control over operational parameters in multiple bioreactors in parallel.

TABLE 1

Exemplary Characteristics of Standard Bioprocess Development Tools

| | Experiments/ Week | Oxygenation/ Oxygen limited Cell density (OLCD) | Available Analysis | Operating Protocols |
|---|---|---|---|---|
| Microtiter Plate | 50000- 10,000 | OTR = 0.007 mol/L/h $k_L a$ = 0.01/s $1.3 \times 10^9$ cells/mL | End point, binary selection | One, open loop |
| Shake Flask | 50-100 | OTR = 0.035 mol/L/h $k_L a$ = 0.05/s $6.3 \times 10^9$ cells/mL | Time series, no material balance | One or two, open loop |
| PIB Array | 20-50 | OTR = 0.14 mol/L/h $k_L a$ = 0.2/s $2.6 \times 10^9$ cells/mL | Time series, no material balance | Multiple, closed loop controlled. |
| Bench scale bioreactor | 1-5 | OTR = 0.35 mol/L/h $k_L a$ = 0.49/s $6.3 \times 10^{10}$ cells/mL | Time series, material balances | Multiple, closed loop controlled. |

Specifically, the invention provides a microscale bioreactor system including a microscale bioreactor comprising a growth chamber and providing environmental control within the chamber. The device may also comprise a plurality or array of microscale bioreactors 10 (see, e.g., FIG. 1), integrated and fabricated into a single module, which may be operated in parallel, wherein each bioreactor comprises at least one growth chamber and wherein each bioreactor provides environmental control within the chamber. The availability of a large number of bioreactors operating in parallel offers a number of unique advantages. For example, the microbioreactor array makes it possible to (i) systematically evaluate the effects of varying one or more of a large number of parameters (e.g., dissolved oxygen, temperature, nutrient composition, pH, etc.) on any phenotypic characteristic of interest, e.g., growth rate, metobolite production or compound biotransformation ability, etc., of a particular strain and/or (ii) systematically evaluate the characteristics (e.g., metabolite production) of a large number of different strains while holding environmental conditions constant.

Various embodiments of the present invention benefit from simple, parallel fabrication of complex functions using molding techniques, and are easy to use, highly functional and inexpensive. For example, in one aspect, the PIB device comprises a bioreactor constructed by molding device layers from molds cast from device masters fabricated by computer numerically controlled milling, and further comprising and supporting miniature-to-macroscopic interfaces to pneumatic actuation lines. In one embodiment, the PIB device of the present invention comprises a growth chamber, at least one environmental variable sensor within the growth chamber to measure or sense environmental properties and characteristics including, but not limited to, dissolved oxygen, pH, density measurements, chemical analysis, e.g., using Raman spectroscopy, etc., a fluid reservoir and a fluid injector to inject fluid from the fluid reservoir into the growth chamber. In another embodiment, the PIB device comprises a control unit or computing system, wherein the control unit monitors and processes data from at least one environmental variable sensor, and controls the environmental conditions by injecting fluids into the growth chamber of the PIB device, or by changing the composition of the actuation gas into the peristaltic oxygenating mixer of the PIB device.

Integrated Bioreactor

FIG. 2a depicts an exemplary embodiment of the present invention, wherein the integrated bioreactor 10 is a pneumatically actuated system comprising a peristaltic oxygenating mixer 2, a metered fluid injector 4, a growth chamber 6, and at least one environmental variable sensor 8 located within the growth chamber 6. The metered fluid injector 4 injects fluid from the fluid reservoir to the growth chamber 6. The growth chamber 6 is mixed by the oxygenating mixer 2. In one aspect of this embodiment, the bioreactor 10 comprises a base reservoir 40 and an acid reservoir 42, wherein the metered fluid is passed from its respective reservoir 40, 42 into the growth chamber 6. The sensor 8 in the growth chamber 6 may detect and/or measure various environmental variables of the growth chamber 6 including, but not limited to, pH, oxygen levels, temperature, nutrient content, carbon-dioxide levels, medium conductivity, medium dielectric permeability, optical density, cell density, etc. In one embodiment, the device may comprise a plurality of sensors to detect/measure a plurality of environmental conditions (e.g., an oxygen sensor to measure oxygen levels and a pH sensor to measure pH, both located within the growth chamber 6). In another embodiment, sensor measurements are taken at predetermined intervals after fluid injections, during injections, before injections and in between injections, or any other time before, during or after the bioreactor run.

In another embodiment, the PIB device provides feedback control of environmental conditions, wherein the PIB device may detect an environmental variable within the growth chamber and implement an appropriate response to maintain or change the conditions in the chamber. In one embodiment, the implementation of an appropriate response is the injection of acid into the growth chamber. In another embodiment, the implementation of an appropriate response is the injection of base into the growth chamber. In yet another embodiment, the implementation of an appropriate response may be no further injections, or an injection of other fluids including, but not limited to, nutrients. Implementation of an appropriate response may occur according to a predetermined scheme selected prior to the beginning of the bioreactor run, or a scheme adjusted during the bioreactor run either automatically or manually, dependent upon the feedback from the bioreactor. For example, in one embodiment, the device comprises a control unit (not shown) connected to the PIB device wherein the control system monitors the environmental conditions of the growth chamber 6 through the environmental variable sensors 8, 44 located within the growth chamber 6. The sensors signals convey measurement or detection data back to the control unit. In one aspect of this exemplary embodiment, the control unit may be a computing system, wherein the computing system is preprogrammed to regulate the pH of the growth chamber 6 to remain between 6.9 and 7.1. The control unit may receive a pH measurement from the sensor 8 in the growth chamber that the pH has fallen below 6.9, and may activate the controls of the bioreactor 10 to inject a metered amount of base from the base reservoir 42 into the growth chamber 6 to raise the pH. Alternatively, the control unit may be programmed to maintain a pH of 7 in the growth chamber 6 for three hours, and then reduce the pH of the growth chamber 6 to 6. The control unit would send an appropriate metered injection of acid to the growth chamber 6 to lower the pH, dependent upon the pH measurement taken by the pH sensor and transmitted back to the control system. The control unit may initially send one injection of acid or base from the corresponding reservoir 40, 42, wait for the pH sensor 8 in the growth chamber 6 to detect and transmit a new pH measurement to the control unit. The control unit may then decide whether and when to send subsequent injections.

In yet another embodiment, the device is adaptive. The injected volume, buffer capacity of the medium in the growth well, and/or the exact volume of the medium may not be known before the bioreactor run. Therefore, pH measurements may be taken at regular or predetermined time intervals. In one aspect, an acid or base may only injected at every other interval. The intervals, wherein the acid or base is not injected, are used to estimate the change in pH due to the chemical, or biological, process occurring in the medium. In one aspect, the natural change in pH with time is estimated by $dpHdt=(pH(t1))-pH(t0))/(t1-t0)$, wherein t=time and t0 is the time of the previous pH measurement and t1 is the time of the most recent pH measurement. For the intervals wherein an acid or base is injected, the change in pH due to a single injection is estimated, taking into account the change in pH due to the previously estimated chemical or biological process in the medium. In another aspect, $pHinj=(pH(t2)-pH(t1)-dpHdt*(t2-t1)/N$, wherein N is the number of injections and t2 is the time of the pH measurement that occurs after the injection and t1 is the time of the pH measurement that occurred before the injection. This estimate of the change in pH due to a single injection is used to calculate the number of injections necessary to achieve the desired pH change. As time passes and more measurements are taken by the environmental variable sensors, the estimates of the change in pH due to the chemical or biological process, and the estimates of the change in pH due to an injection become more accurate. In one aspect, it is assumed that these parameters change slowly and the estimates may be low-pass filtered (e.g., filtered using a butterworth filter) to reject noise. Furthermore, in some aspects, the estimates may not be reliable (e.g., at the beginning of an experiment, if the pH is near the limits of the pH sensor, or if the pH is in a range where a small addition of acid or base will cause a large pH change). In those aspects, the maximum number of injections (or amount of metered/injected fluid) may be limited to prevent overshoots or undershoots. In other aspects, the change in pH due to injection may be less than expected (e.g., a valve does not open properly). In those aspects, the control unit assumes that there was no injection and adjusts its estimates accordingly.

In other various embodiments, the fluid injector 4 may inject acid from an acid reservoir 42 into the growth chamber 6 a strong acid such as hydrochloric acid (HCl), nitric acid ($HNO_3$), sulfuric acid ($H_2SO_4$), hydrobromic acid (HBr), hydroiodic acid (HI), perchloric acid ($HClO_4$), or combinations thereof. Similarly, the fluid injector may inject a strong base into a reservoir (and then subsequently into the growth chamber) such as lithium hydroxide (LiOH), sodium hydroxide (NaOH), potassium hydroxide (KOH), rubidium hydroxide (RbOH), cesium hydroxide (CsOH), calcium hydroxide $(CaOH)_2$, strontium hydroxide $(Sr(OH)_2)$, barium hydroxide $(Ba(OH)_2)$, ammonium hydroxide ($NH_4OH$), ammonia ($NH_3$) dissolved in water, or a combination thereof. In other aspects, the fluid injector injects a weak acid, a weak base, or variations or combinations thereof.

Figure 2B:
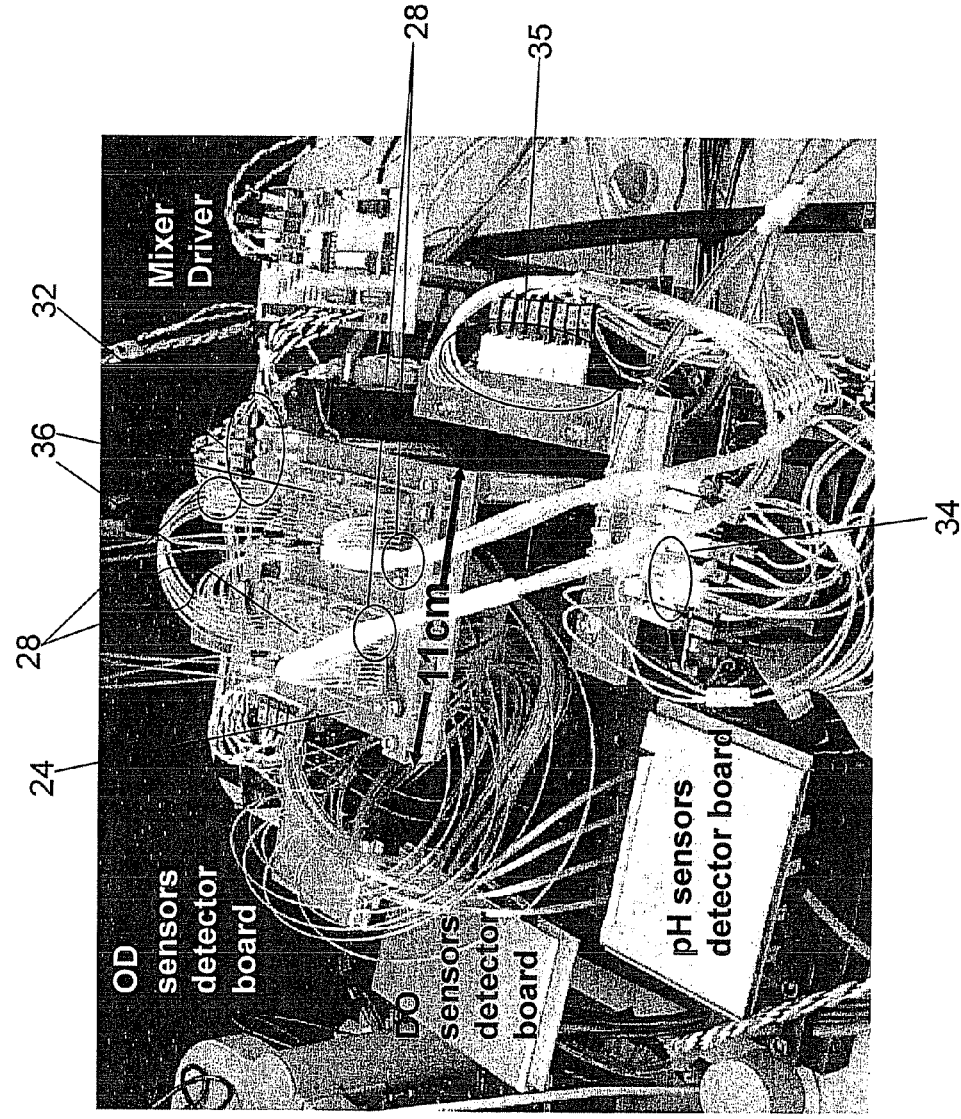
FIG. 2b is a photograph of another embodiment of the present invention.
Figure 2C:
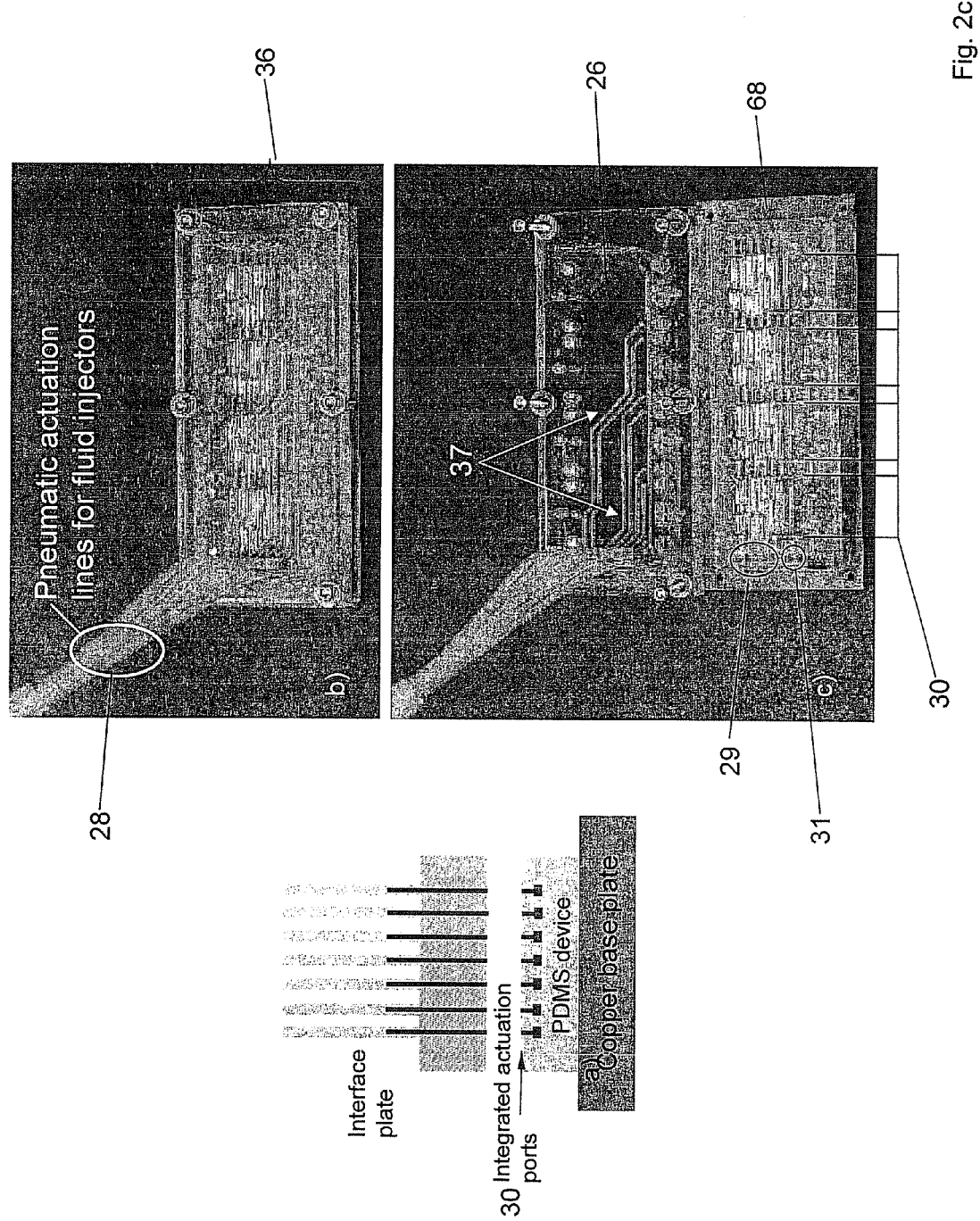
FIG. 2c is a photograph depicting the manifold integrated in an interface plate, according to another embodiment of the invention.

Furthermore and as shown in FIGS. 2b and 2c, different embodiments of the invention comprise at least one supporting interface module 36 connecting the bioreactor 10 to at least one pneumatic actuation line 28 by an actuation port 29,30,31. For example, in one embodiment, the PIB device is pneumatically actuated, wherein the pneumatic actuation occurs through the actuation lines connected to an interface module 36. The actuation line provides pressure from external sources to the various components of the bioreactor. The PIB device may be sandwiched within an interface module 36 further comprising a thermally conducting secondary base plate 68 and an interface plate 26. In one aspect, the interface plate comprises a manifold 37 to route the at least one pneumatic actuation line 28 to at least one actuation port 29,30,31 of the PIB device. The channels of the integrated manifold terminates in a hole pattern that aligns with an actuation port pattern on the PIB device. Therefore, in one aspect, the pneumatic actuation lines can be interfaced to the PIB device in a single step. This eliminates the need to plug individual pneumatic lines into each actuation port, and results in simple alignment and device mounting. In another aspect, the actuation port further comprises a molded gasket 66 (see FIG. 2a). The molded gasket 66 may facilitate face sealing of the interface plate. The interface plate 26 may be any rigid material including, but not limited to, polymer, metal, polycarbonate, PMMA, or any combination thereof. In one embodiment, the interface plate 26 is a transparent thermoplastic. In another embodiment, the interface plate 26 is a polycarbonate.

In yet another embodiment, the PIB device of the present invention comprises a base plate, wherein the base plate supports the bioreactor 10 (or bioreactor array) and may further facilitate the transmission of information from the at least one environmental variable sensor to the control unit (e.g., wherein the sensor is optical and the base plate further serves as the mechanical support to hold fiber bundles to interface the control unit with the optical sensors). In different embodiments, the base plate 24 may be a thermally conductive material including, but not limited to, polymer or metal, or any combination thereof. In one embodiment, the base plate 24 is copper. In yet another embodiment, the base plate 24 is temperature controlled.

In another embodiment, the PIB device comprises at least one fluid filling port 38, wherein fluids are injected into reservoirs or growth chamber through the filling port 38. In one aspect of this embodiment, the fluids are injected via syringe and needle.

In other certain aspects, the reservoirs may be filled with fluids while the at least one pneumatic actuation line is pressurized, allowing for priming of the fluid injectors 4 before filling the growth chamber 6. Priming the device allows for reliable operation and also allows for recovery of samples at the completion of the bioreactor run, without injecting excess acid or base.

Growth Chamber

In certain embodiments of the invention, the bioreactor comprises a growth chamber 6 for culturing cells, and a means for providing oxygen and fluid to the chamber 6 at a concentration sufficient to support cell growth. In certain embodiments of the invention, the growth chamber 6 has an interior volume of less than 1 ml. In certain embodiments of the invention, the chamber 6 has an interior volume of less than 500 µL. In certain other embodiments of the invention, the chamber 6 has an interior volume of less than 200 µL. In certain preferred embodiments of the invention, the interior volume of the growth chamber 6 is between 50 µL and 100 µL inclusive. In certain preferred embodiments of the invention, the interior volume is approximately between 80 µL and 100 µL inclusive. In other embodiments, the interior volume is approximately 7.5 µL, or approximately 10 µL, or approximately 5 µL. In another embodiment, the growth chamber has a flat form factor (i.e., the depth of the growth well is much smaller than its lateral dimensions). For example, the depth may be approximately 500 µm, while the lateral dimensions are approximately 1.5 cm.

Small interior volumes and flat form factor offer a number of advantages. For example, they permit efficient gas-liquid contacting to control the level of dissolved oxygen ("DO"). Small interior volumes within the growth chamber 6 also imply smaller diffusion times, which aids in exchange of gases. In addition, microscale bioreactors having interior volumes in the range of between 5 µL and 50 µL or between 50 µL and 100 µL may be more easily produced using microfabrication than those with larger interior volumes.

Sensors

As mentioned above, the PIB device of the present invention comprises at least one environmental variable located within the growth chamber to measure and/or detect chemical or biological properties of the growth chamber. In another embodiment, the device comprises a plurality of sensors to measure and detect different environmental variables within the growth chamber. For example, in one aspect, the PIB device comprises a chemical ion sensitive field effect sensor to measure the pH of the growth chamber. In another aspect, the PIB device may comprise an optical sensor to measure and detect oxygen levels within the growth chamber. For example, in one embodiment, an optical sensor made from Platinum-octaethyl-porphyrine in a polystyrene matrix may be located within the growth chamber to measure oxygen levels. The fluorescence of the Pt-OEP is quenched in the presence of oxygen and the fluorescence lifetime is measured to estimate the dissolved oxygen concentration. In other embodiments, various combinations of different sensors may be used to transmit signals back to the control unit with measurement information, e.g., biological and/or chemical analyses.

In one embodiment, the pH sensor 8 measures the pH of the contents of the growth chamber 6 using fluorescent dye. The dye may be immobilized onto supporting substrates which are then attached to the inside of the growth chamber 6. Excitation and interrogation of the sensor 8 occurs through fiber bundles with integrated optical filters. In another embodiment, a plurality of sensors measure various environmental conditions using fluorescent dyes.

Peristaltic Oxygenating Mixer

Figure 7:
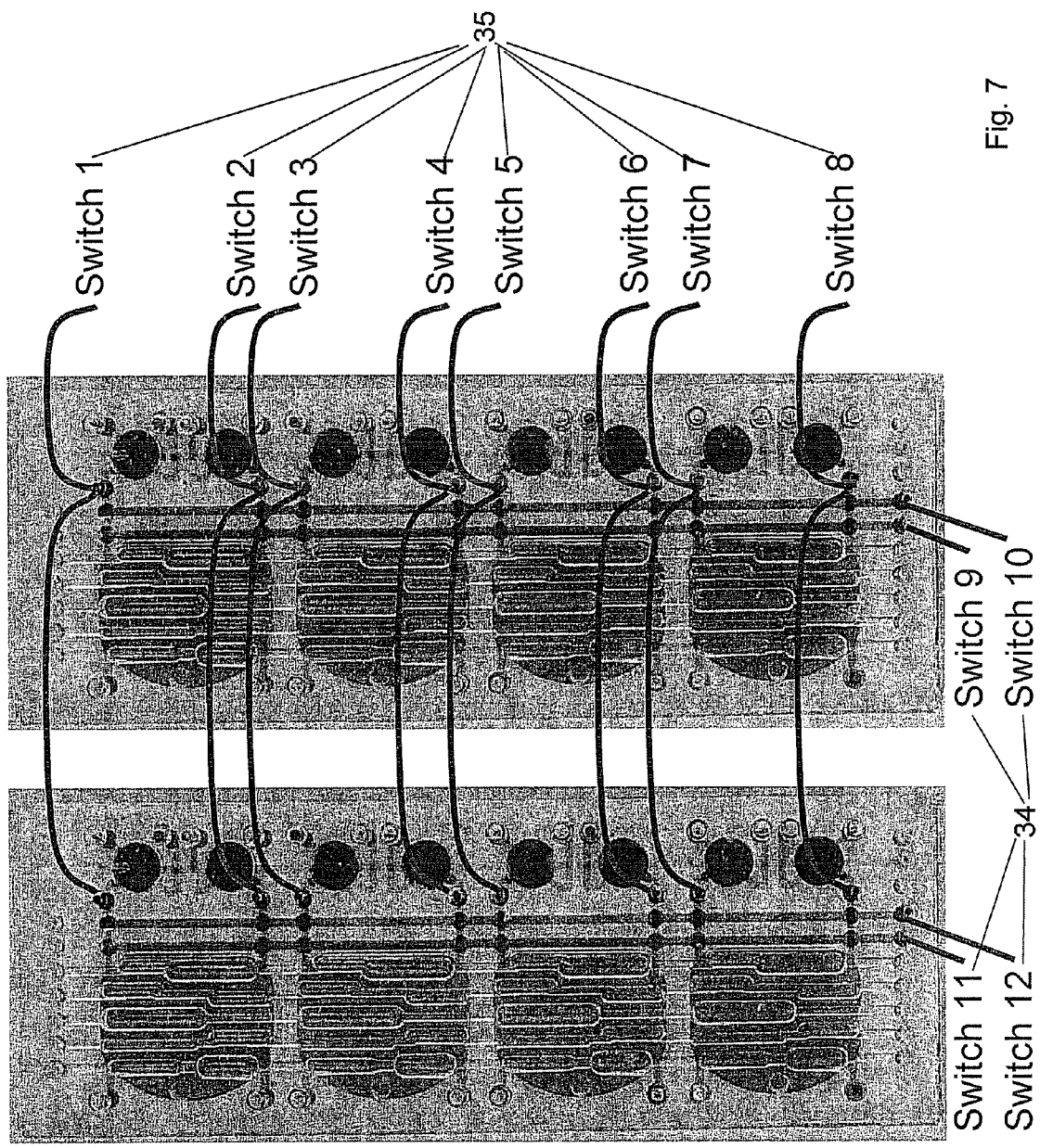
FIG. 7 is a photograph of another embodiment of the present invention, wherein the bioreactor array has individual control over sixteen fluid injectors with twelve pneumatic switches, wherein the first fluid injector valve is individually controlled across modules and the other injector valves are shared along the module.

In one embodiment, the peristaltic oxygenating mixer 2 is the subject of the recent Patent Application Publication No. 20050106045, entitled "Peristaltic Mixing and Oxygenation System" and incorporated herein by reference. In various aspects, the mixer 2 has one or more peristaltic mixing tubes 16. Mixing may be accomplished by approximating peristalsis in the growth chamber 6 by pressurizing the mixing tubes 16 in a propagating pattern, which generates a circulating flow across and around the growth chamber 6. In one aspect (as shown in FIG. 2b and FIG. 7), the present invention comprises a solenoid switch 32 in communication with each mixing tube via at least one actuation line 28 and actuation port 29, to drive and/or pressurize the peristaltic oxygenating mixer 2. For example, in one embodiment, the oxygenating mixer 2 comprises five mixing tubes 16, and the mixing tubes 16 are pressurized two at a time, in a propagating pattern. The mixer 2 therefore creates a homogenous mixture of starting materials and/or reactants and achieves a high oxygen transfer rate without introducing bubbles into the growth chamber. This allows online measurement of the optical density which can be used to calculate an online estimate of the growth rate. In one embodiment, the mixing tubes 16 are shared across multiple bioreactors 10 such that only one solenoid switch 32 is required to actuate a mixing tube 16 across multiple bioreactors 10.

In various embodiments, the dissolved oxygen in the PIB device may be controlled by changing the oxygen concentration in the actuation gas. For example as shown in FIG. 13, the peristaltic oxygenating mixer 2 of various embodiments of the PIB may further comprise a gas mixing reservoir 54 with a source of oxygen enriched air 56 and a source of oxygen neutral or deficient air 58, and a gas switch 55. In one embodiment, the gas mixing switch 55 is a single 3-way solenoid switch 60. In another embodiment, the gas mixing switch 55 is driven by simple digital electronics. The source of oxygen neutral or deficient air 58 may be connected to the normally open port of the gas mixing switch 55. The source of oxygen enriched air 56 may be connected to the normally closed port of the gas mixing switch 55. The switch 55 is toggled between the normally closed and normally open ports to control the dissolved oxygen concentration in the PIB device 10. For example, in one embodiment, the switch 55 is toggled at a frequency of between approximately 0.1 and 3 Hz and the oxygen concentration of the gas at the output of the gas mixing reservoir 54 could be determined by the duty cycle of the switching. The oxygen concentration of the gas at the output of the gas mixing reservoir 54 would be: $C_{out}=C_{normallyclosed}*d+C_{normallyopen}*(1-d)$, where d is the duty cycle of the gas mixing solenoid switch 55. Further to this example, if the duty cycle is 25%, the concentration at the output of the reservoir is 500%*0.25+100%*0.75=200%, where the % denotes percentage of dissolved oxygen concentration in equilibrium with air. The duty cycle is computed using a proportional-integral-derivative (PID) control algorithm whose parameters can be determined by one of ordinary skill in the art.

Figure 11:
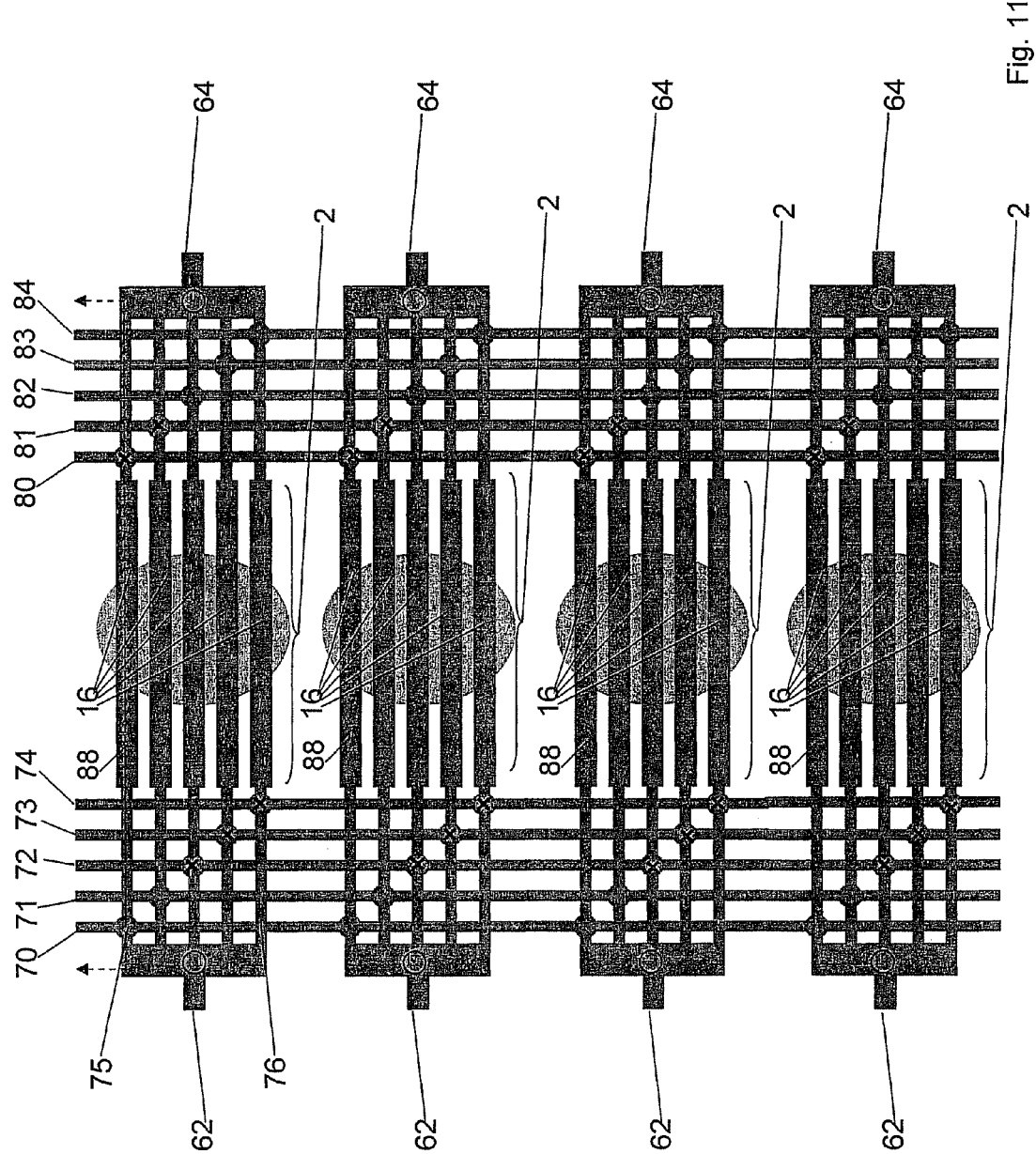
FIG. 11 is a schematic diagram of one embodiment of the present invention, which allows individual control over dissolved oxygen.
Figure 12:
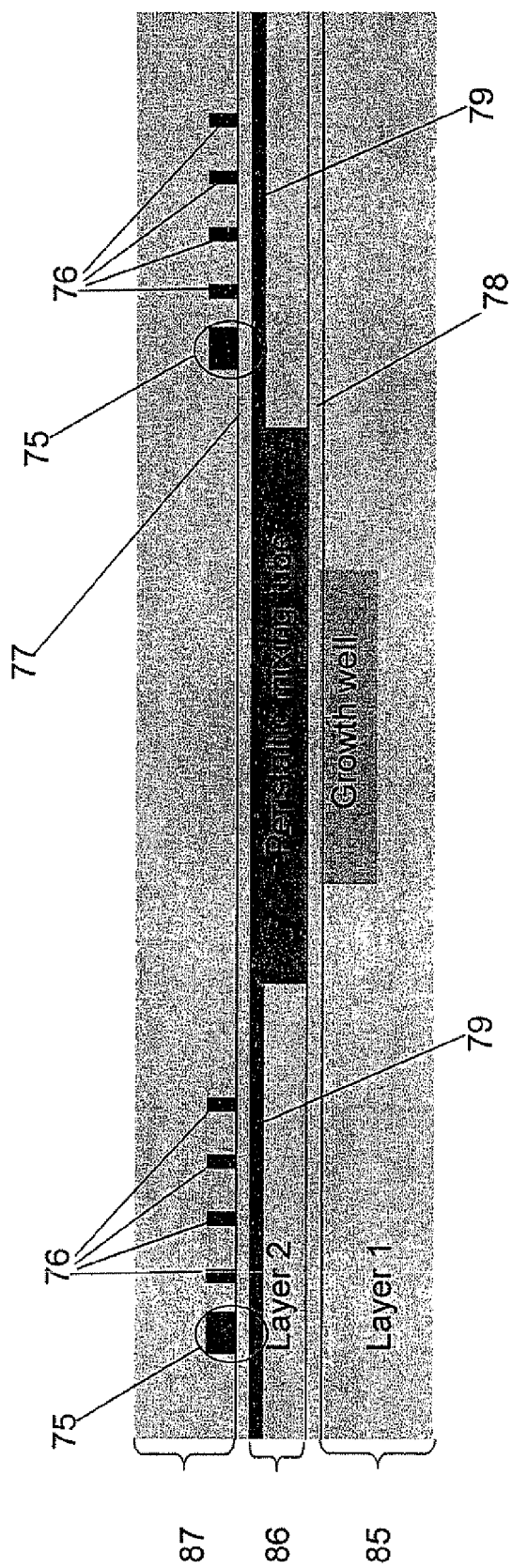
FIG. 12 illustrates a cross section of the device according to one embodiment that allows individual control over dissolved oxygen.

In another embodiment, the dissolved oxygen in each PIB device within an array is controlled independently, without requiring individual solenoid valves 32 for each mixing tube 16 in each independent peristaltic oxygenating mixer 2. FIGS. 11 and 12 depict one configuration of the present invention which allows individual control over dissolved oxygen. For example, the mixing tubes 16 of the peristaltic oxygenating mixer 2 can be isolated for each growth chamber 6 with actuation pressure of the control valves 75 for each mixing tube 16 shared across the isolated peristaltic oxygenating mixers 2 for each bioreactor 10. In one embodiment, the actuation pressure is shared through integrated control valve actuation lines 76. Each peristaltic oxygenating mixer 2 has an independent gas mixture inlet 62 and gas mixture outlet 64, which allows independent dissolved oxygen control. An independent gas mixing reservoir 54 and gas mixing switch 55 with an independently controllable duty cycle provides an independently controllable oxygen concentration to the independent gas mixture inlets 62. The gas mixture inlet 64 is at a higher pressure than ambient. The gas mixture outlet 64 is at approximately ambient pressure. The deflection of a peristaltic mixing tube 16 can be controlled by opening and closing the control valves 75 on either side of the mixing tube 16, formed by the mixing tube control channel 79, mixing tube control valve membrane 77, and mixing control valve layer 87. For example, to pressurize only the top peristaltic mixing tube 88 of each peristaltic oxygenating mixer 2 in the array, the mixing tube control valve actuation lines 70, 81, 82, 83, 84 are vented, opening the valves 75 in pneumatic communication with the actuation lines 70, 81, 82, 83, 84 while actuation lines 71, 72, 73, 74, 80 are pressurized closing the valves 75, in pneumatic communication with actuation lines 71, 72, 73, 74, 80. This puts the top mixing tube 88 in pneumatic communication with the gas mixture inlet port 62 and the remaining mixing tubes 16 in pneumatic communication with the gas mixture outlet port 64. Because actuation of the valves 75 can be shared across multiple bioreactors, only 2*M solenoid switches are required for actuation of multiple bioreactors, each with M peristaltic mixing tubes.

The PIB device or array may be constructed from three layers 85, 86, 87 with molded features including but not limited to growth chambers 6, microchannels 18, 79 and actuation lines 76, bonded together with membranes in between each layer. Regions where a membrane section is suspended above a channel and the opposite surface of the membrane is in pneumatic or hydraulic communication with an actuation line form the injector valves 20 and mixer control valves 75.

Fluid Injector

In another embodiment, the fluid injector 4 is comprised of a fluid reservoir 14 sealed with a flexible membrane 12, and an injector channel 18 gated by valves 20, wherein the valves 20 meter fluid into the growth chamber 6. In one aspect, the fluid reservoir 14 may be hemispherical in shape and pressurized by introducing air or hydraulic pressure in a pressure chamber 22 above the fluid reservoir 14. This generates positive pressure to drive fluid into the growth chamber 6. The pressure chamber 22 may be controlled by the control unit, and become pressurized through at least one actuation line 28 connected to the bioreactor 10 through an actuation port 33. Other embodiments may further comprise at least two independently controllable fluid injectors 4, both in fluidic communication with the growth chamber 6. In one aspect, the reservoir 14 can hold approximately 15-25 µL of fluid.

Metering of the fluid into the fluid reservoir 14 or growth chamber 6 is accomplished by actuating the metering valves 20 via the actuation lines 28 and actuation ports 30,31 in a pattern to distribute a set amount of fluid into the growth chamber 6. For example, a fluid plug was injected by actuating the metering valves and pressure reservoir using the sequence 100-1, 101-1, 001-0, 011-0, 111-0, where the first three digits indicate the pressurization state of the metering valves, the first digit being the pressurization state of the valve closest to the growth chamber 6, and the last digit after the dash, the pressurization state of the pressure chamber 22 and fluid reservoir 14. wherein '1' indicates a pressurized and closed valve or pressurized pressure chamber 22 and '0' indicates an unpressurized and open valve or unpressurized pressure chamber 22.

In one aspect, the actuation sequence 100-1, 101-1, 001-0, 011-0, 111-0 injects approximately 270 nL of fluid into the growth chamber 6. The amount of fluid injected by one cycle of the actuation sequence is determined by the channel dimensions and size of the center metering valve. The total amount of fluid injected may be increased by repeating the actuation sequence to cause multiple fluid plug injections in sequence and may be predetermined or controlled through the control unit based upon the environmental variable measurements returned from the at least one sensor 8, 44 located within the growth chamber 6. For example, the amount of base injected may be determined by the control unit upon receiving a pH measurement from the sensor 8 in the growth chamber 6 that is too acidic.

In another aspect, actuation pressure and solenoid switches 34 for the metering valves 20 may be shared along a column of bioreactors 10. In one embodiment of this aspect, two of the metering valves 20 of each injector 4 share a common actuation port 31 and are pressurized/vented together by the same solenoid switches 34 and a third metering valve 20 of each injector 4 have independent actuation ports 30 and are independently controlled by solenoid switches 35 for each row of bioreactors. The independently controlled valve may be closest to the fluid reservoirs 14, as shown in FIG. 1 or to the growth chamber 6.

In other embodiments, the apparatus of the present invention may have individual control over multiple fluid injectors 4 (e.g., FIG. 7 shows control over sixteen fluid injectors and forty-eight total valves with twelve pneumatic switches).

In another embodiment, a thin membrane 12 forms the moving component of the valves 20. Regions where a membrane section is suspended above a channel with rounded cross-section and the opposite surface of the membrane is in pneumatic or hydraulic communication with an actuation line form the injector valves 20. For example, when an integrated actuation line 27 crosses a fluidic channel 18 with rounded cross section and the width of the integrated actuation line 27 is increased at the intersection such that the cross-sectional area of the freely suspended membrane above the fluidic channel is increased forms a valve structure wherein the valves "pinch" closed the channel, with rounded cross-section, when the pressure above the membrane is increased, deflecting it into the channel and forming a seal preventing fluid communication between either side of the valve.

Various issues may arise when constructing a device with metering valves as described above. For example, valves may remain closed when they should be venting. One of ordinary skill in the art can understand various methodologies to avoid sticking valves. In one embodiment, the PIB device incorporates surfactant (e.g., 1% weight per weight of Pluronic F-108) to reduce valve metering errors. In another embodiment, the PIB device is "refreshed" every several seconds wherein, for example, the two valves closest to the reservoirs in a four reactor array are opened and the pressure chamber above the reservoirs is pressurized for approximately 100-500 ms. After the pressure chamber is pressurized, the two valves closes to the reservoirs are closed. This process opens the two valves closest to the reservoir while the valve closest to the growth chamber remains closed to prevent fluid from entering the chamber. This helps prevent sticking because the valve sticking becomes worse the longer a particular valve remains continuously closed.

In one aspect, hydraulic pressure is used to fill the pressure chamber. Hydraulic pressure may reduce the amount of gas that diffuses through the membrane to form bubbles. In other aspects, bubble formation underneath the membrane may be avoided by adding a dilute concentration of fluid to the pores of the fluid injector. For example, in one aspect, the pores of the injector comprise a gel. In another aspect, the pores comprise 0.02% Carbomer.

Inoculum Preparation Chamber

In a further embodiment of the present invention, the PIB device comprises an inoculum preparation chamber (not shown), wherein the inoculum chamber is filled with a starter culture and allows the culture to grow. When the culture reaches an appropriate cell density, the entire contents of the inoculum chamber is injected into the growth well. In another embodiment, the inoculum preparation chamber is a reservoir (e.g., 40 or 42), wherein the inoculum is passed from the reservoir into the growth chamber 6.

Control Unit

The control unit processes the environmental variable sensor signals and provides the appropriate pneumatic pressures to actuate the components of the PIB device, including the peristaltic oxygenating mixer and the fluid injectors. In one embodiment, the control unit comprises an analog to digital conversion unit, a digital processing unit, a digital driver, and a solenoid switch driver. The analog to digital conversion unit digitizes the analog sensor signals which are then processed digitally using software algorithms running on a digital computer in order to obtain dissolved oxygen concentration, pH, and optical density measurements. Measured values of the dissolved oxygen concentration are used in PID control algorithm to determine the required duty cycle of the gas mixing switch 55. Measured values of the pH are used by an adaptive pH control algorithm which determines the number of acid or base injections required to maintain the pH at the setpoint. The control outputs from the digital processing unit are digital (TTL) signals which activate the solenoid switch driver. The activated solenoid switch driver causes the normally closed port of the pneumatic solenoid switches to be connected to the common port of the switch. For the pneumatic switches controlling the metering valves, where the normally closed port is at ambient pressure and the normally open port is at a high (ie. 12 psi) pressure, activation of the solenoid switch opens the metering valve.

Device Construction

Figure 15:
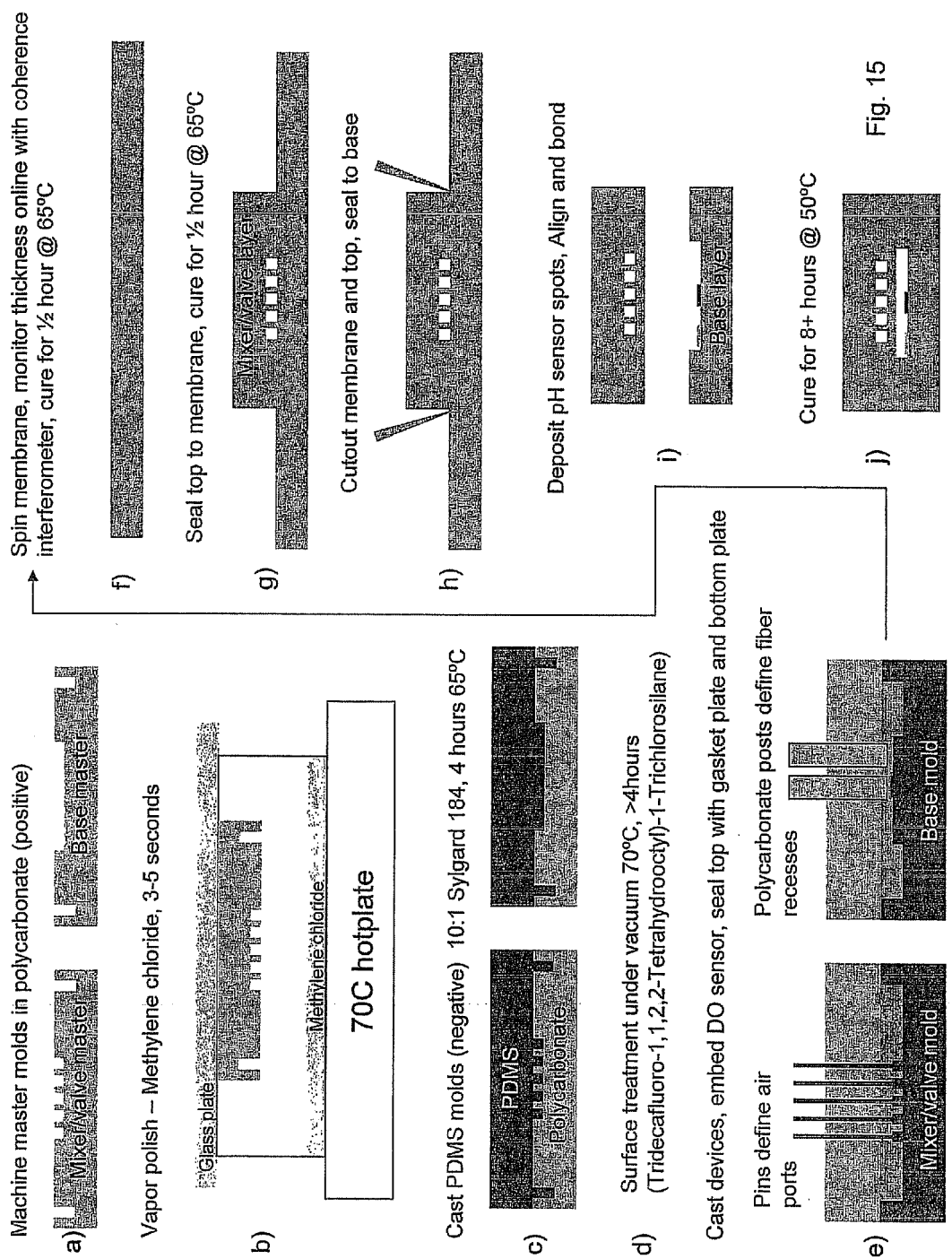
FIG. 15 illustrates the fabrication process flow for fabricating one embodiment of the present invention.

In various other embodiments, the PIB device of the present invention is constructed using a simple molding process. FIG. 15 illustrates the fabrication process flow according to one embodiment of the invention. For example, the PIB device of the present invention may be constructed using a polycarbonate mold transfer process. Construction steps for the device may include:

Device structure design, wherein the design may be converted into instructions for a computer numerically controlled milling machine.

Machine replicas of device layers, e.g. top and bottom layer. In one embodiment, the layers are machined from polycarbonate. These layers create a positive mold.

Vapor polish the mold to smooth machine marks and obtain optically clear surfaces.

Cast negative molds. In another embodiment, negative molds are cast using polydimethylsiloxane (PDMS).

Fully cure molds.

Surface treat the molds to prevent adhesion of the device and molds. For example, the PDMS molds are surface treated to prevent adhesion of the PDMS used to make the device with the PDMS mold. Surface treatment of a PDMS mold may be accomplished using (Tridecafluoro-1,1,2,2-Tetrahydroocytl)-1-Trichlorosilane) vapor at approximately −25 psig vacuum and 70 degrees Celcius.

Cast the devices in the mold and optionally embed sensors into the mold, and seal the top surface with a previously machined top mold, further defining the actuation ports of the interface plate.

Partially cure the device. In one aspect, the device is cured for approximately 1 hour at 65° C.

Coat a surface-treated silicon wafer, so as to prevent adhesion of the wafer with coating. For example, PDMS may be spin coated onto a surface-treated wafer. The thickness of the PDMS membrane is monitored as it is spun using low coherence interferometry.

Partially cure the coated membrane. In one aspect, a PDMS membrane is cured for approximately 30 minutes at 65° C.

Seal the top of the device to the membrane.

Partially cure the device. In another aspect, the device is partially cured for approximately 30 minutes at 65° C.

Cut the top half from any excess membrane.

Attach at least one sensor to the inside of the bottom half of the device.

Seal the top half and membrane to the bottom half of the device.

Fully cure the device. In yet another aspect, the device is fully cured for approximately 12 hours at 45° C.

In yet another embodiment, all PDMS is used at the recommended mixing ratio of 10:1, polymer:cross-linking agent.

A simple fabrication process like the one described above constructs a device comprising components with widely ranging lateral dimensions (e.g., 100 µm to 1.5 cm), depths (e.g., 100 µm to 1.7 mm), and profiles (e.g., square, round, etc.). Conventional photolithography techniques struggle to make features deeper than 100 µm-300 µm and are typically limited to rectangular profiles. Different profiles will allow a device containing various elements including fluid injection systems and peristaltic oxygenation mixers to be sealed properly.

The embodiments described above demonstrates how the PIB device of the present invention introduces integrated fluid injection and mixing devices to enable control over environmental variables in a miniature parallel integrated bioreactor array system.

In another embodiment, the present invention is a method of controlling the environmental conditions of a bioreactor comprising providing fluid injection and high oxygen levels to the growth chamber of the bioreactor to enable pH control in the growth chamber. In one aspect, the method comprises providing fluid injection to the growth chamber based upon measurements transmitted from a pH sensor within the growth chamber to a control unit external to the bioreactor. For example, the method of controlling the environmental conditions of a bioreactor may comprise providing fluid injections of base or acid to the growth chamber. The method may further comprise mixing the growth chamber to enhance oxygen levels.

In yet another embodiment, the present invention is a method of controlling environmental conditions within a microscale bioreactor comprising providing a bioreactor constructed using a simple molding process, wherein the bioreactor comprises a growth chamber, a reservoir in fluidic communication with the growth chamber, a metered fluid injector to pass metered amounts of fluid from the reservoir into the growth chamber, and a sensor located within the growth chamber, wherein the sensor measures the pH properties of the growth chamber. In one aspect of this method, the bioreactor further comprises a peristaltic oxygenating mixer, wherein the mixer mixes the contents of the growth chamber. In still other embodiments, the present invention is a method controlling environmental conditions within a microscale bioreactor, comprising controlling the oxygenation concentration in the bioreactor. In one aspect, the bioreactor comprises a peristaltic oxygenating mixer, and the mixer further comprises a gas switch which controls the oxygenation concentration in the mixer. Still further, the present invention a method of controlling environmental conditions within an array of microscale bioreactors, comprising providing independent control over oxygenation concentration in each microscale bioreactor.

It should be noted that where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

Applications And Extensions

The devices of the invention find particular use as small scale culture vessels (e.g., tens to hundreds of microliters) for cells, e.g., bacteria, fungi, and/or other eukaryotic cells. Thus preferred embodiments of the devices address the needs for mixing, oxygenation and pH control that exist in this context. In this regard it is noted that the chambers may include a variety of additional components, e.g., sensors for ions or various substrates such as glucose, waveguides to collect light, e.g., for spectroscopy, etc. (See, e.g., C. E. Miller, "Chemometrics for on-line spectroscopy applications—theory and practice," Journal of Chemometrics, vol. 14, pp. 513-528, 2000). The devices may be interfaced to equipment for collecting data from the sensors (e.g., computers such as PCs or work stations or any sort of microprocessor, spectrometers, etc.) to form an overall system for culturing cells and monitoring the culture.

The multichamber devices described herein offer the ability to conduct multiple fermentations (by which is meant culturing cells in general, not restricted as to cell type or culture conditions) under conditions of substantially identical oxygenation and mixing. This allows the comparison of multiple different cell strains in parallel. In addition, other parameters such as substrate concentrations, pH, etc., can be systematically varied. Thus the invention provides a method of selecting a strain that produces a desired product or degrades an unwanted compound comprising steps of (a) culturing a plurality of different strains, each in an individual chamber of a device of the invention; (b) measuring the amount of the desired or unwanted product in each of the chambers; and (c) selecting a strain that produces an optimum amount of a desired product or degrades a maximum amount of the unwanted compound. The invention further provides a method of selecting a bioprocess parameter comprising steps of (a) culturing an organism type in a plurality of chambers in a device of the invention, wherein the value of the bioprocess parameter varies within different chambers and wherein the organism produces a product or degrades a compound; (c) monitoring biomass in each of the chambers; and (d) identifying the value of the bioprocess parameter that results in optimum biomass, optimum product formation, or optimum compound degradation. Once optimal strains and/or parameters are selected using the devices of the invention, scale-up to larger vessels can be performed.

The devices of the invention may be used to culture essentially any type of cell including microorganisms such as bacteria (e.g., eubacteria, archaebacteria), filamentous or non-filamentous fungi (e.g., yeast), protozoa, and also plant cells, insect cells, mammalian cells, etc. Bacteria may be aerobes, facultative anaerobes, or anaerobes and include, but are not limited to, members of the following genera: *Escherichia, Enterobacter, Streptomyces, Azotobacter, Erwinia, Bacillus, Pseudomonas, Klebsiella, Proteus, Salmonella, Serratia, Shigella, Rhizobia, Rhodococcus, Vitreoscilla,* and *Paracoccus*. (See the Web sites with URLs www.bacterio.cict.fr/eubacteria.html and www.bacterio.cict.fr/archaea.html for lists of bacteria that may be used.). Yeast include, but are not limited to, members of the genera: *Saccharomyces, Schizosaccharomyces, Moniliella, Aureobasidium, Torulopsis, Candida, Trigonopsis, Trichosporon, Torulopsis, Zygosaccharomyces,* and *Yallowia*. Insect cells, e.g., cells that support the growth of baculovirus such as *Spodoptera frugiperda* sf9 cells (see, U.S. Pat. No. 4,745,051) may be used. Such cells are particularly useful for production of recombinant proteins. Mammalian cells including, but not limited to, Chinese hamster ovary (CHO) cells, human embryonic kidney (HEK) cells, COS cells etc., may be used. In certain preferred embodiments of the methods the cells are of a type that is currently used in commercial bioprocesses.

The cells may be newly isolated or identified naturally occurring strains or variants, which may also be referred to as mutants. The cells may be selected, e.g., for a desirable phenotype. The cells may be genetically modified, e.g., using recombinant DNA technology. For example, cell or strain variants or mutants may be prepared by introducing appropriate nucleotide changes into the organism's DNA. The changes may include, for example, deletions, insertions, or substitutions of, nucleotides within a nucleic acid sequence of interest. The changes may also include introduction of a DNA sequence that is not naturally found in the strain or cell type, e.g., a sequence coding for a reporter molecule or a sequence coding for or providing a template for transcription of any molecule of interest. One of ordinary skill in the art will readily be able to select an appropriate method depending upon the particular cell type being modified. Methods for introducing such changes are well known in the art and include, for example, oligonucleotide-mediated mutagenesis, transposon mutagenesis, phage transduction, transformation, random mutagenesis (which may be induced by exposure to mutagenic compounds, radiation such as X-rays, UV light, etc.), PCR-mediated mutagenesis, DNA transfection, electroporation, etc.

One of ordinary skill in the art will be able to select appropriate culture media and environmental conditions for any particular cell type. Parameters such as oxygen delivery, temperature, and pH, etc., may be varied as appropriate. In addition, the microfermentor properties such as surface characteristics, vessel size, etc., may be modified depending upon the features of the particular cell type to be cultured. Parameters that may be varied (e.g., to identify optimum parameters) include, but are not limited to: growth medium (carbon/energy source (e.g., glycerol, succinate, lactate, and sugars such as, e.g., glucose, lactose, sucrose, and fructose), nitrogen source, precursors, and nutrients such as vitamins and minerals, salts, etc.), temperature, pH, redox potential, mixing rate, ionic strength, osmotic pressure, water activity, hydrostatic pressure, concentration of inducers and repressors, etc. Any of these parameters may be varied in different ways in individual chambers operating in parallel. In addition, the devices can be used to screen for compounds that have particular effects on cells, e.g., in screening for pharmaceutical agents, evaluating the effects of potential toxins, etc.

More generally, the invention may be used in any of a variety of applications involving chemical reactions, in which mixing and supplying reagents and/or removal of products is desired, e.g. "lab-on-a-chip" (Figeys, D., and Pinto, D., *Anal. Chem.* 72A:330-35, 2000), micrototal analysis systems (µTAS) (Jakeway, S., et al., *Fresenius J. Anal. Chem.* 336: 525-39, 2000; Ransey, J., van den Berg, A., (eds.) *Micro Total Analysis Systems* 2001. Boston: Kluwer Acad. 2001), etc. It is noted that the invention may also provide for heat exchange, by appropriately cooling or heating the gas or fluid in the hollow cavities. While the invention is likely to be most useful for applications involving the mixing of small volumes, it is not limited to that.

EXAMPLES

Example 1

Materials And Methods

Using the device as shown in FIG. 1, four sulfite oxidation experiments were run simultaneously wherein the pH control was activated only in two reactors. The device was mounted into an interface module and the fluid injector actuation lines were activated. Approximately 20 µL of 1M HCL was injected into the acid reservoir, and 20 µL of 1M NaOH was injected into the base reservoir, using a syringe and fine gauge needle. The acid/base lines were primed such that a small amount of acid/base was injected into the empty reservoirs. An identical solution of 100 mM of sodium sulfite in 100 mM dibasic phosphate was injected into all four reactors via a syringe and fine gauge needle. Since sulfite is a weak base with pKa=6.8, it has a buffering capacity of around neutral pH. When sulfite is oxidized into sulfate, the buffer capacity is lost and the pH decreases. The peristaltic oxygen mixers were activated in each of the bioreactors. Before the solutions were injected, the pH of both sodium sulfite and dibasic phosphate was initially adjusted to 6.7 by adding HCl. The pH of the reactor solutions was adjusted to 7 by activating the control unit, which individually injected the appropriate amount of base into each of the four separate reactors via the fluid injectors as described above. The control unit monitored and injected fluids at regular intervals of the first and third reactor while the control unit did not inject fluid into the second and fourth reactor.

Results

Figure 5:
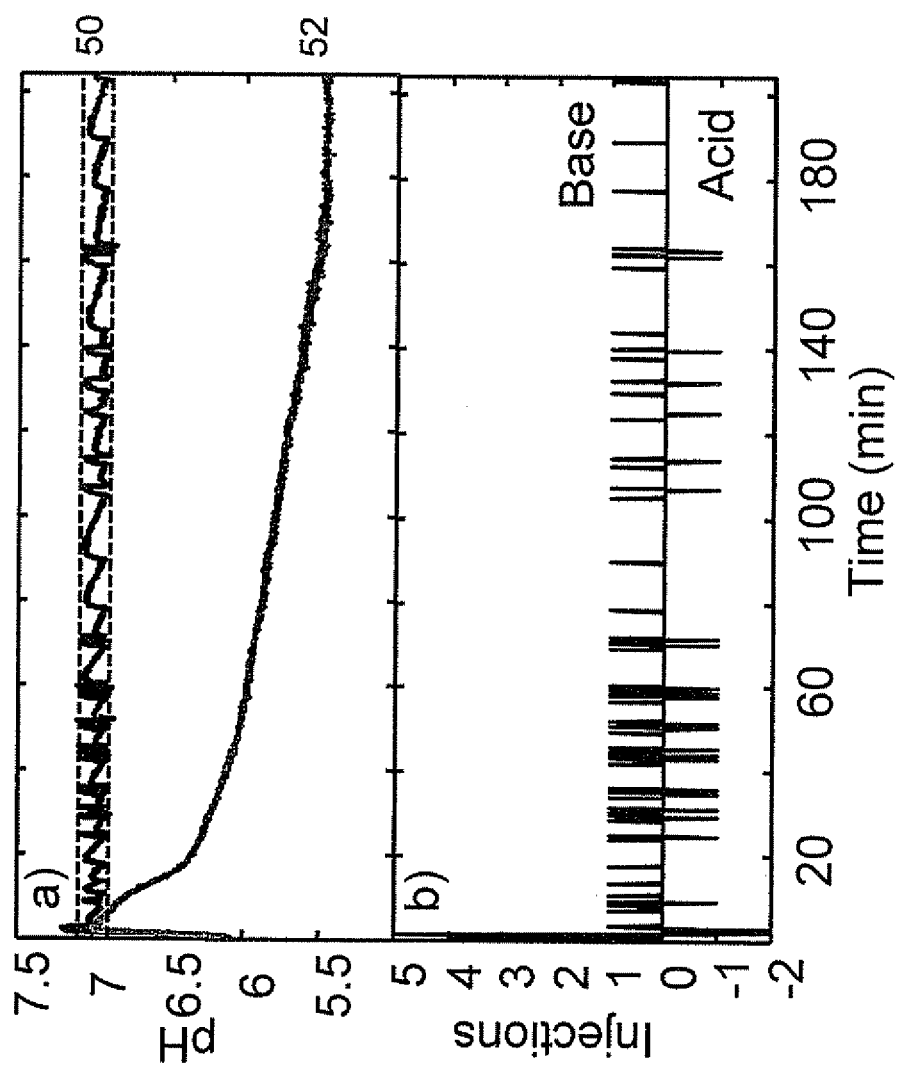
FIG. 5 is a plot of pH with and without control over time, during a 100 mM sulfite oxidation in 24 mM phosphate.

The pH of the solution in all of the reactors was measured throughout the experiment. At the end of the experiment, the pH of the first reactor 50 (comprising active fluid injections) was 6.9, and the pH of the second reactor 50 (not comprising active fluid injections) was 5.85. FIG. 5 shows the pH versus time of two of the simultaneous sulfite oxidation experiments for two of the reactors. Initially the pH for all wells was brought to 7.0. Then, as the sulfite oxidation reaction proceeded, the pH decreased in the uncontrolled case as the concentration of sulfite, which acts as a weak base, decreased. With pH control, the pH was maintained at 7.0+/−0.1.

Example 2

Materials And Methods

Using the device shown in FIG. 1, reactors were run wherein fluid injections supplied acid and base to the growth chamber (filled with 100 mM phosphate buffer), and a pH sensor measured the pH of the growth chamber after each injection. The first reactor received an injection of 270 nL acid (1M HCl) and base (1M NaOH) every two minutes for two hours.

Results

FIG. 4a shows pH versus time wherein the markers indicate the pH measurement after every second pH injection. FIG. 4b is a zoom view of a portion of the pH versus time graph shown in FIG. 4a. FIG. 4b shows that the injected base is mixed into the growth chamber within fifteen seconds. This is indicated by the sharp steps in pH after each injection. The markers of FIG. 4 indicate every other acid or base injection. FIG. 4c shows agreement with a direct alignment with a conventionally measured titration curve, verifying the accuracy of the estimated injected volume (e.g., 270 nL). Aligning this titration curve with a conventionally measured titration curve allowed estimation of the 270 nL+/−50 nL injected volume. This was larger than the 80 µL design volume due to bulging the membrane under the metering valves.

Example 3

Materials And Methods

The fluid injectors shown in FIGS. 1 and 2 consist of a 16 µL hemispherical fluid reservoir sealed with a flexible membrane, which can be deflected by pressurizing the chamber above, and an injector channel gated by three pneumatically actuated membrane pinch valves, which meter the fluid. Pressurizing the fluid reservoirs served to help open the pinch valves and ensure injection against backpressure. The mixing tubes and pinch valves were actuated pneumatically as described above, and the mixing tubes and two metering valves are shared for the economy of the pneumatic switches.

Mixing was accomplished by approximating peristalsis in the 85 μL growth wells by pressurizing the mixing tubes two at a time in a propagating pattern, generating a circulating flow across and around the well.

The devices were fabricated using two molded PDMS (Dow Corning, Sylgard 184) layers and a 70 μm thick PDMS membrane, bonded with a partial cure bond. Master positive molds with the required variable depth and cross-section features were CNC machined in polycarbonate and negative casts of these masters were used to mold the devices. Fluorescence based optical sensor spots (Presens, HP5) were used to measure pH and calibrated against standard buffer solutions, similar to those of N. Sita, A. Zanzotto, P. Boccazzi, A. J. Sinskey, M. A. Schmidt, K. F. Jensen, "Monitoring of Cell Growth, Oxygen, and pH in Microfermentors," in Micro Total Analysis Systems 2002, Kluwer Academic Publishers, pp. 7-9: November 2002.

The devices were pneumatically actuated using a computer-controlled array of solenoid switches (Lee Company, LHDA). The mixing tubes were actuated with 3-4 psi air at an update frequency of 25 Hz with the pattern: '00011', '00110', '11000', '10001'. The injector valves were operated at 12 psi with the sequence: '100', '101', '001', '011', '111'. In both cases, the '1' indicates a closed valve (pressurized) and '0' indicates an open valve (vent).

The acid and base reservoirs were filled with 1M HCl and 1M NaOH. Injector lines were primed before filling the growth wells. Mixing was demonstrated by synchronously imaging the spread in the color change of a 0.3 mM bromothymol blue pH indicator solution with each mixing cycle, titrations were carried out on a 100 mM solution of phosphate buffer, and pH control was demonstrated using a solution of 100 mM sodium sulfite and 24 mM phosphate. Actuation pressure was 3 psi with a 25 Hz update rate. Peristalsis was to the left.

Results

Figure 3:
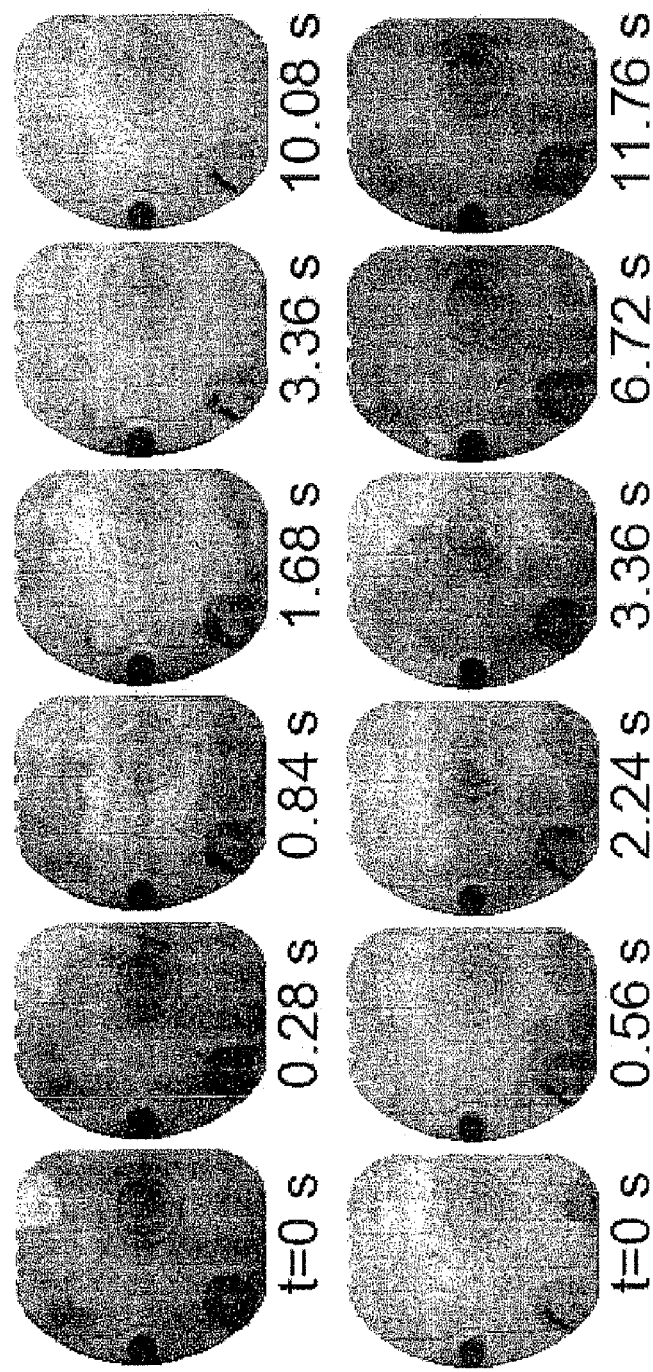
FIG. 3 is a timed image sequence of a growth well showing mixing after an acid injection and a base injection according to one embodiment.
Figure 6:
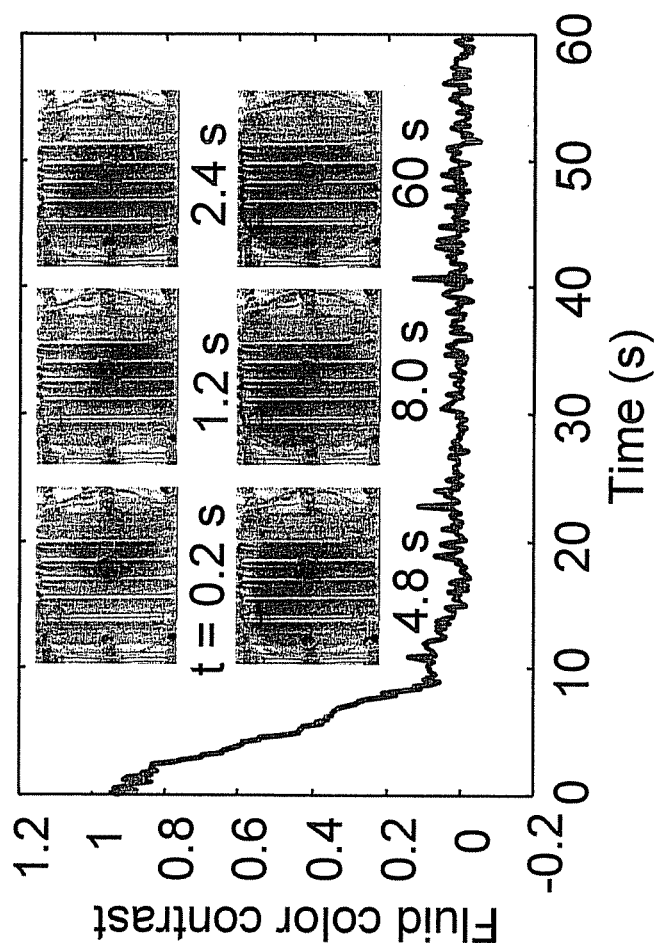
FIG. 6 is a timed image sequence and plot of fluid color contrast over time of the peristaltic mixing of an earlier generation device without fluid injectors.

Image sequences that demonstrate mixing and capture the flow pattern within the growth well are shown in FIG. 3. FIG. 3 is an image sequence after an acid (1M HCl) injection (top) and a base (1M NaOH) injection (bottom). Mixing was completed in less than 15 seconds. Peristaltic mixing in an earlier device is shown in FIG. 6, without fluid injectors. Fluid color contrast is the normalized maximum difference between pixel intensities, corrected for image artifacts. Zero indicates fully mixed. This was consistent with FIG. 4b, where sharp pH steps after injections indicated homogenization in less than 20 seconds.

Example 4

Materials And Methods

Two experiments using one embodiment of the PIB device of the present invention were conducted on separate days, and the following comparisons were made: a) growth with pH control versus growth without pH control; growth with longer pH control versus growth with shorter pH control; and growth with longer pH control with oxygen enriched air versus growth with longer pH control without oxygen enriched air.

The strain used was *E. coli* FB21591 Kanamycin resistant derivative of K12. The medium was modified Luria-Bertani (+10 g/L yeast extract, +5 g/L $K_2HPO_4$, 40 g/L glucose). Common conditions were the temperature (T=37° C.) and the same inoculum.

In the first of the two experiments, three reactors were operated with no pH control and five reactors were operated with pH control. The five pH controlled reactors were initially adjusted to a pH of 7, and thereafter were regulated with injections of 1.6M of $NH_4OH$ and 1M HCl. All of the reactors in the first experiment were aerated with air.

Figure 8:
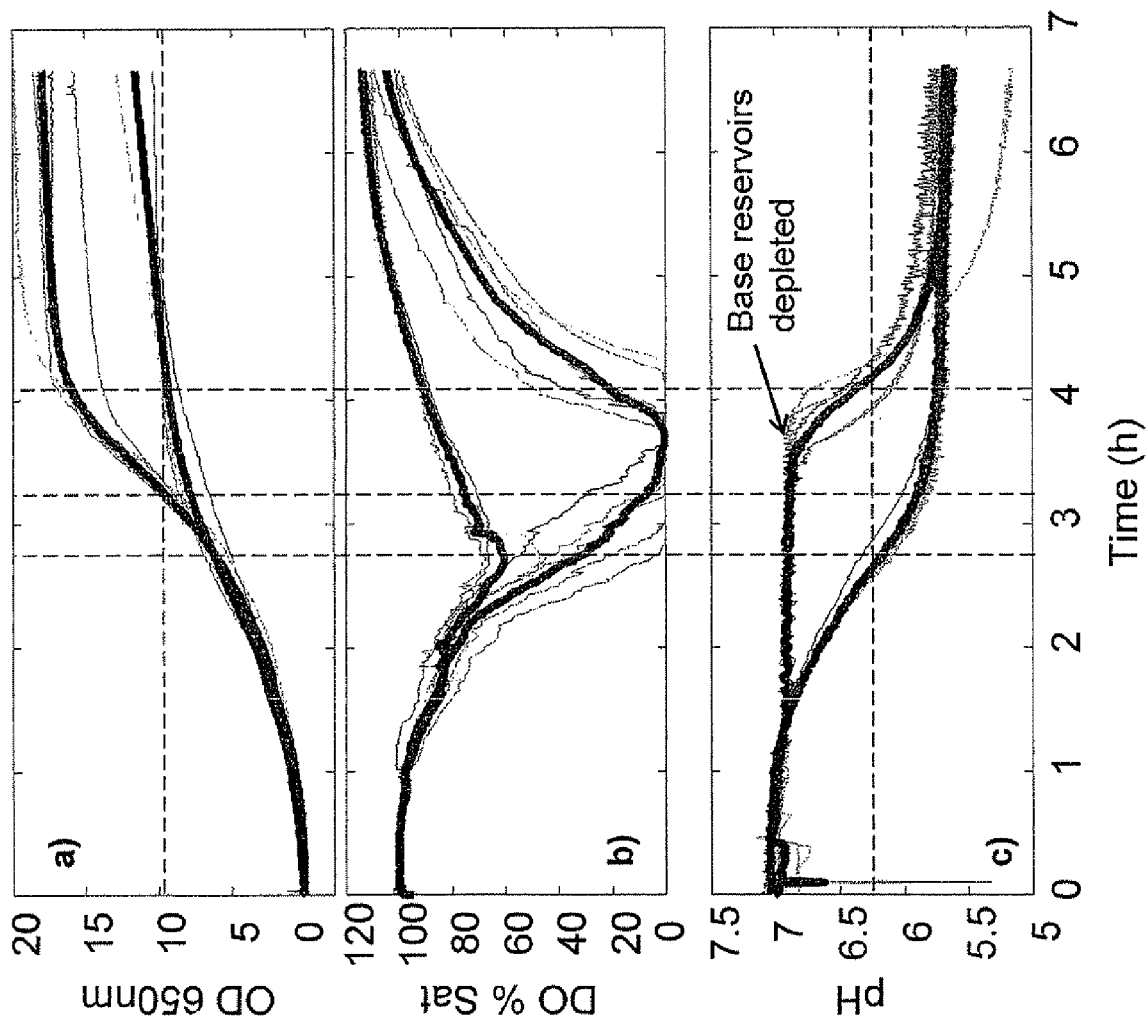
FIG. 8a is a plot of optical density over time of one embodiment of the present invention, wherein pH controlled reactors are compared with uncontrolled reactors.
FIG. 8b is a plot of dissolved oxygen over time of another embodiment of the present invention, wherein pH controlled reactors are compared with uncontrolled reactors.
FIG. 8c is a plot of pH over time, wherein pH controlled reactors are compared with uncontrolled reactors.

FIG. 8a plots optical density (approximately linear to cell density) 650 nm versus time for the first experiment. The top curve represents the cell density of the reactors operated with pH control. The bottom curve represents the cell density of the reactors operated without pH control. The reactors operated with pH control show an enhanced cell growth of approximately 60%.

FIG. 8b plots dissolved oxygen (% saturation) over time. The top curve represents the reactors operated without pH control. The bottom curve represents the reactors operated with pH control.

FIG. 8c plots pH over time of the first experiment. The top curve represents cell growth within the reactors operated with pH control. The bottom curve represents cell growth within the reactors operated without pH control. The top curve shows that there was a stronger and more steady cell growth with pH control, at least until the base reservoirs were depleted (at approximately 3½ hours).

In the second of the two experiments, each reactor was operated with pH control, with an initial adjustment to a pH of 7. The reactors were thereafter regulated with injections of 2.4 M $NH_4OH$ and 1M HCl. Four reactors were aerated with air. Four reactors were aerated with 50% $O_2$ as necessary to keep DO>40%.

Figure 9:
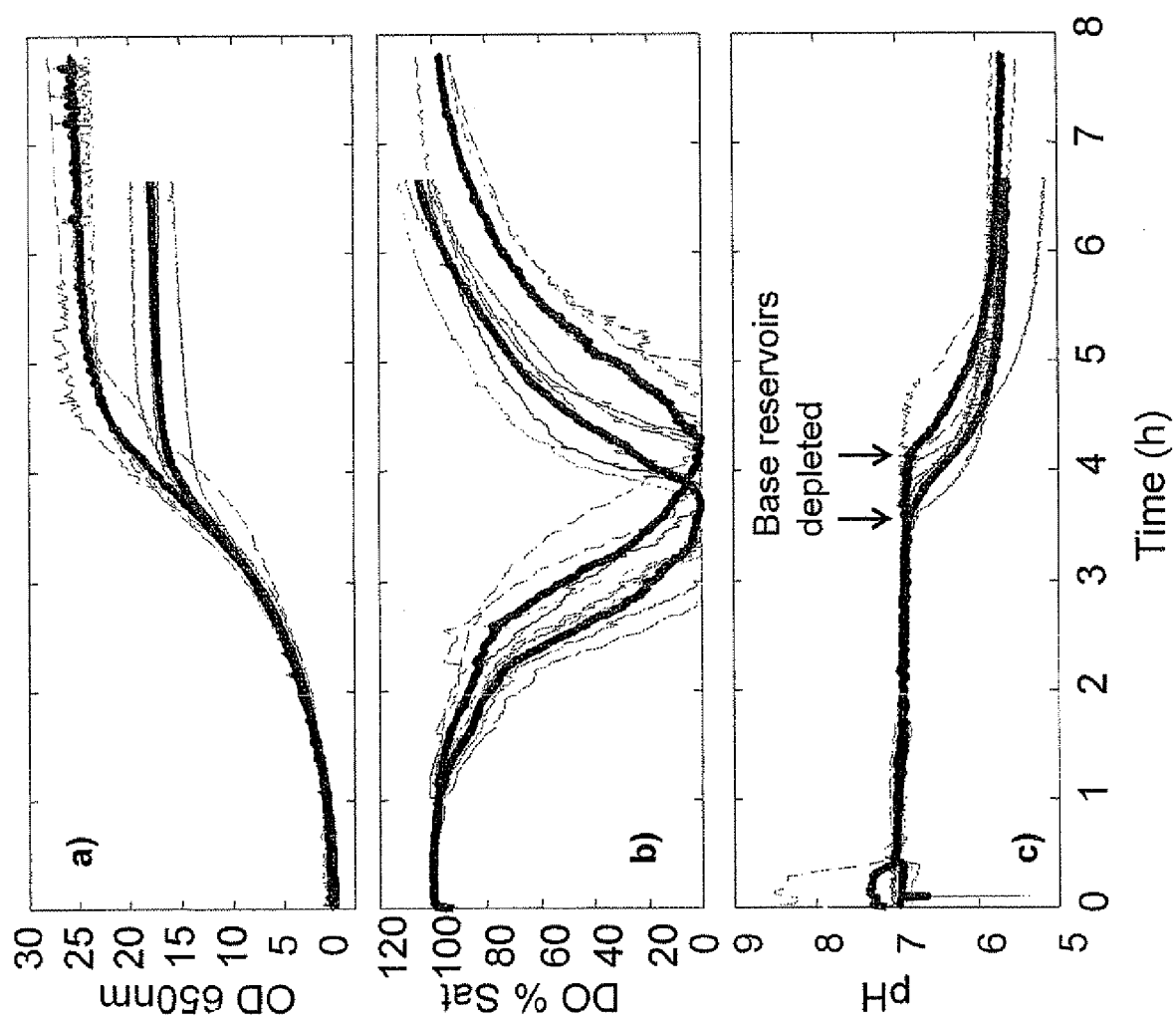
FIG. 9a is a plot of optical density over time of one embodiment of the present invention, wherein pH controlled reactors with an increased base molarity are compared with pH controlled reactors with a set level of base molarity.
FIG. 9b is a plot of dissolved oxygen over time of another embodiment of the present invention, wherein pH controlled reactors with an increased base molarity are compared with pH controlled reactors with a set level of base molarity.
FIG. 9c is a plot of pH over time, wherein pH controlled reactors with an increased base molarity are compared with pH controlled reactors with a set level of base molarity.

FIG. 9a plots the optical density at 650 nm versus time for the first and second experiment. The top curve represents the reactors operated with pH control at 2.4 M NH4OH, aerated with air from the second experiment. The bottom curve represents the reactors operated with pH control at 1.6 M NH4OH, aerated with air, from the first experiment. The increased molarity of the base increases cell growth both over the same time, and for a longer amount of time.

FIG. 9b plots the dissolved oxygen (% saturation) over time for the second experiment. The top curve represents the reactors run with pH control at 1.6 M NH4OH, aerated with air, from the first experiment. The bottom curve represents the reactors run with pH control at 2.4 M NH4OH, aerated with air, in the second experiment.

FIG. 9c plots the pH over time of the first and second experiment. The top curve represents the reactors run with pH control at 2.4 M NH4OH, aerated with air, from the first experiment. The bottom curve represents the reactors run with pH control at 1.6 M NH4OH, aerated with air, from the first experiment. By increasing the molarity of the base, the amount of time that the PIB device could maintain pH control over the growth chamber increased.

Figure 10:
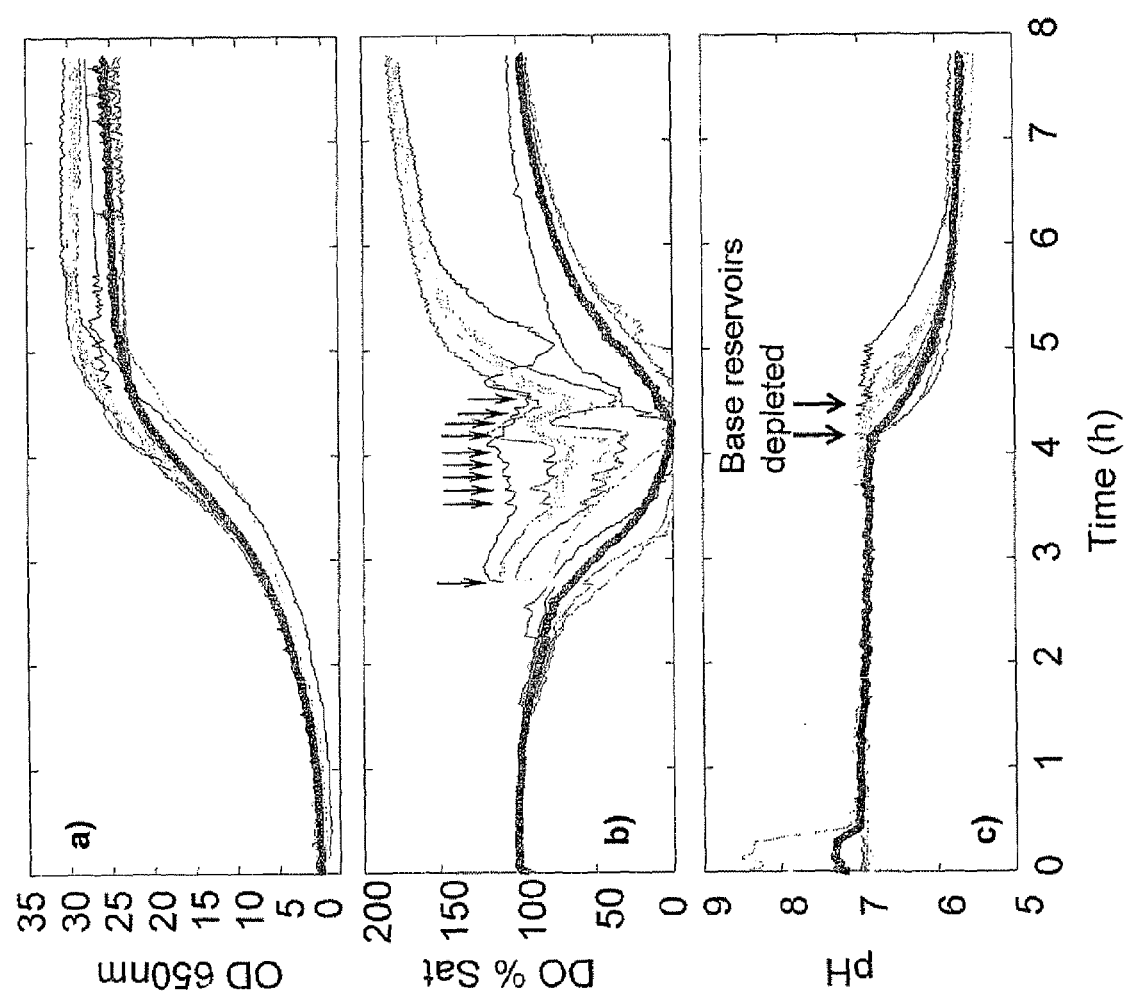
FIG. 10a is a plot of optical density over time of one embodiment of the present invention, wherein pH controlled reactors aerated with 50% $O_2$ are compared with pH controlled reactors aerated with air.
FIG. 10b is a plot of dissolved oxygen over time of another embodiment of the present invention, wherein pH controlled reactors aerated with 50% $O_2$ are compared with pH controlled reactors aerated with air.
FIG. 10c is a plot of pH over time, wherein pH controlled reactors aerated with 50% $O_2$ are compared with pH controlled reactors aerated with air.

FIG. 10a plots the optical density (650 nm) versus time from the second experiment between the reactors aerated with 50% $O_2$ and the reactors aerated with only air. The top curve represents the reactors aerated with 50% $O_2$. The bottom curve represents the reactors aerated with air only. FIG. 10b plots the dissolved oxygen (% saturation) over time between the two sets of reactors from the second experiment. FIG. 10c plots the pH over time between the two sets of reactors.

These two experiments show that in certain embodiments, the PIB device of the present invention may allow longer control over the pH conditions within the growth chamber by increasing the base molarity and increasing oxygenation. Furthermore, replicates of the experiments correlate strongly, and the various apparatus and methods of the present invention are reproducible.

Example 5

Pneumatic actuation was accomplished through the use of miniature 3-way solenoid switches (The Lee Co. LHDA0523111H) driven by standard driver circuits (National Semiconductor, DS3658), and a digital I/O card (National Instruments DAQcard-DIO-24), along with some simple circuitry.

The dissolved oxygen was controlled by varying the oxygen concentration of the peristaltic oxygenating mixer actuation gas. This was accomplished by varying the duty cycle of the solenoid switch, operated between 0.1 and 3 Hz, that connected the humidification reservoirs 56, 58 with either 4 psi compressed air or 4 psi compressed oxygen to the gas mixing reservoir. The duty cycle of the switch was set by a proportional-integral control algorithm whose error signal was based on the minimum dissolved oxygen concentration among the bioreactors in a module that shared a peristaltic mixer.

Figure 14A:
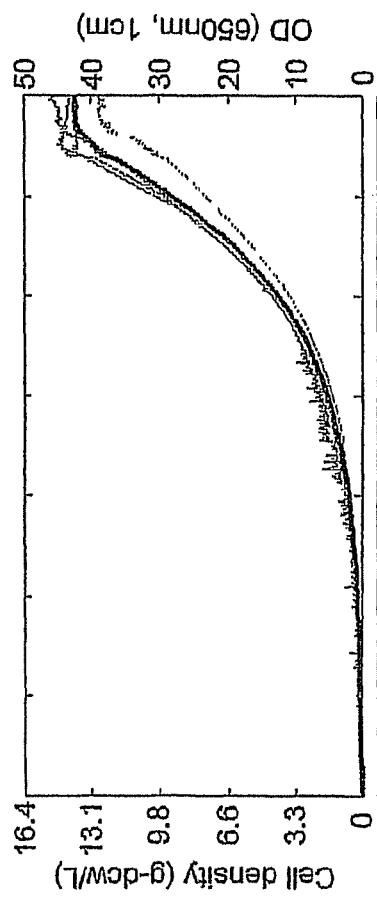
FIG. 14a is a plot of optical density for four E. coli fermentations according ton one aspect of the invention. The heavy line indicates the average of the replicates.
Figure 14B:
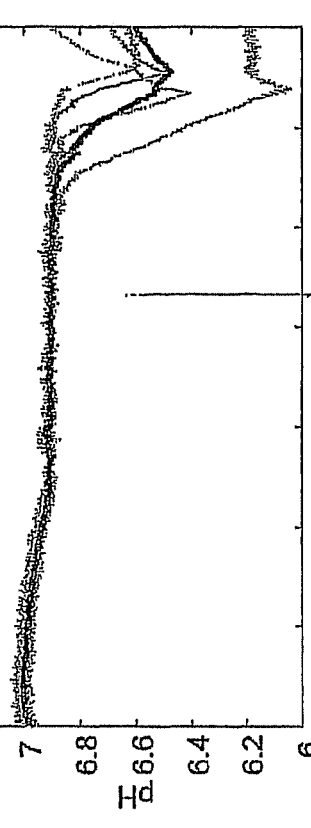
FIG. 14b is a plot of pH over time for the four fermentations of FIG. 14a, showing the control of the pH to approximately 6.9.
Figure 14C:
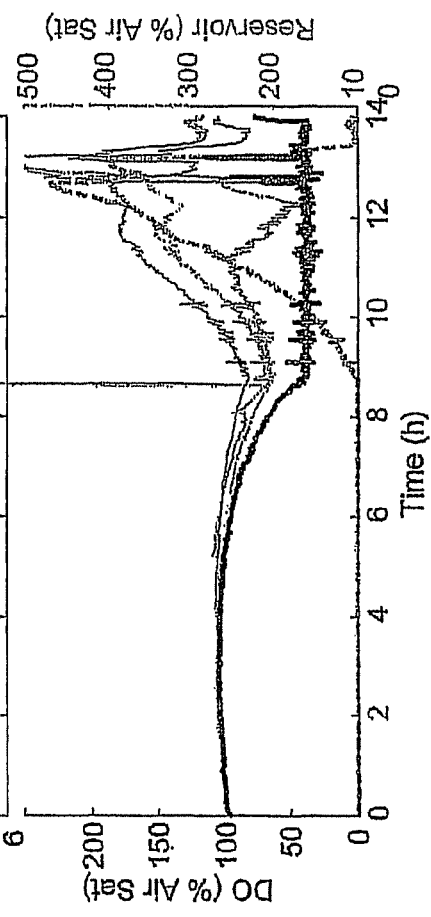
FIG. 14c is a plot of the dissolved oxygen concentration for the four fermentations of FIGS. 14a and 14b, where the heavy line indicates the minimum dissolved oxygen among the four fermentations is controlled at 14% (of the equilibrium concentration with air)

FIG. 14*a* is a plot of optical density for four *E. coli* fermentations. FIG. 14*b* is a plot of the pH over time, showing the control of the pH to 6.9. FIG. 14*c* is a plot of the dissolved oxygen concentration for the four fermentations. The heavy line indicates the mean of the replicates for the cell density and pH, and the minimum of the replicates for the dissolved oxygen (controlled at 40% of the equilibrium concentration with air), respectively.

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims. In the claims articles such as "a,", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. Furthermore, it is to be understood that the invention encompasses all variations, combinations, and permutations in which one or more limitations, elements, clauses, descriptive terms, etc., from one or more of the listed claims is introduced into another claim. In particular, any claim that is dependent on another claim can be modified to include one or more limitations found in any other claim that is dependent on the same base claim. Furthermore, where the claims recite an apparatus, it is to be understood that methods of using the apparatus as described in any of the claims reciting methods are also disclosed, unless it would be evident to one of ordinary skill in the art that a contradiction or inconsistency would arise. It is also to be understood that where the claims recite an apparatus that has particular features or characteristics, the invention encompasses an apparatus comprising means for implementing such features or characteristics. In addition, it is to be understood that any particular embodiment of the present invention that falls within the prior art may be explicitly excluded from the claims. Since such embodiments are deemed to be known to one of ordinary skill in the art, they may be excluded even if the exclusion is not set forth explicitly herein.

We claim:

1. A bioreactor device comprising:
 a growth chamber with an internal volume of less than approximately 10 mL;
 a mixer integrated into an internal surface of the growth chamber;
 at least one integrated fluid injector system to pass metered amounts of a fluid into the growth chamber wherein the fluid affects an environmental variable of the growth chamber;
 at least one sensor located within the growth chamber to measure the environmental variable; and
 a controller configured to control the environmental variable by controlling the at least one integrated fluid injector system,
 wherein the at least one integrated fluid injector system comprises:
 a fluid reservoir;
 a microchannel for providing fluidic communication between the reservoir and the growth chamber;
 a pressure chamber adjacent to the reservoir;
 a flexible membrane, wherein the membrane fluidically isolates the pressure chamber from the reservoir; and
 a valve system for metering fluid into the growth chamber.

2. The device of claim 1, wherein the mixer comprises a peristaltic oxygenating mixer, and wherein the mixer mixes the contents of the growth chamber.

3. The device of claim 1, wherein the pressure chamber applies force to the reservoir, so that the pressure chamber forces fluid contained in the reservoir into the growth chamber.

4. The device of claim 1, wherein the reservoir contains a fluid comprising an acid.

5. The device of claim 1, wherein the reservoir contains a fluid comprising a base.

6. The device of claim 1, wherein the reservoir contains a fluid comprising a nutrient.

7. The device of claim 1, wherein the reservoir contains a fluid comprising a test compound.

8. The device of claim 1, wherein the at least one sensor senses oxygen levels.

9. The device of claim 1, wherein the at least one sensor senses temperature.

10. The device of claim 1, wherein the at least one sensor senses nutrient content.

11. The device of claim 1, wherein the at least one sensor senses carbon-dioxide levels.

12. The device of claim 1, wherein the at least one sensor senses medium conductivity.

13. The device of claim 1, wherein the at least one sensor senses medium dielectric permeability.

14. The device of claim 1, wherein the at least one sensor senses optical density.

15. The device of claim 1, wherein the at least one sensor senses cell density.

16. The device of claim 1, wherein the at least one sensor is fluorescence-based.

17. The device of claim 1, comprising:
 a fluidic interface;
 at least one actuation line;
 and at least one actuation port, wherein the fluidic interface connects the bioreactor to at least one pneumatic actuation line by at least one actuation port on the bioreactor.

18. The device of claim 17, wherein the actuation line provides pressure from a source external to the bioreactor.

19. The device of claim 17, wherein the bioreactor is within the fluidic interface.

20. The device of claim 17, comprising a plurality of actuation ports, wherein the actuation ports exist in a pattern.

21. The device of claim 17, wherein the fluidic interface comprises an interface plate, wherein the interface plate comprises a rigid material.

22. The device of claim 21, wherein the interface plate comprises a material selected from the group consisting of polymer, metal, polycarbonate, PMMA, or any combination thereof.

23. The device of claim 22, wherein the interface plate is sealed to the bioreactor.

24. The device of claim 21, wherein the interface plate comprises a transparent thermoplastic.

25. A bioreactor array comprising:
a plurality of bioreactor devices of claim 17; and
fluidic connections between the actuation lines and the actuation ports, wherein the required number of actuators is less than the number of ports.

26. The device of claim 17, comprising at least one solenoid switch in communication with the bioreactor through the at least one actuation line, wherein the solenoid switch pressurizes the pressure chamber adjacent to the reservoir.

27. The device of claim 1, comprising a base plate, wherein the base plate supports the device.

28. The device of claim 27, wherein the base plate facilitates the transmission of information from the sensor to the controller.

29. The device of claim 27, wherein the base plate comprises material selected from the group consisting of polymer, metal, or any combination thereof.

30. The device of claim 27, wherein the base plate comprises copper.

31. The device of claim 27, wherein the temperature of the base plate is controlled.

32. The device of claim 1, wherein the at least one sensor measures pH at predetermined intervals.

33. The device of claim 1, wherein the at least one sensor measures pH after a metered amount of fluid is passed into the growth chamber.

34. The device of claim 1, wherein the growth chamber has an interior volume of less than 500 µL.

35. The device of claim 1, wherein the growth chamber has an interior volume of less than 200 µL.

36. The device of claim 1, wherein the growth chamber has an interior volume of between approximately 80 µL and 100 µL inclusive.

37. The device of claim 1, wherein the growth chamber has an interior volume of approximately 7.5 µL.

38. The device of claim 1, wherein the growth chamber has an interior volume of approximately 10 µL.

39. The device of claim 1, wherein the growth chamber has an interior volume of approximately 5 µL.

40. The device of claim 1, comprising a chemical ion sensitive fluid effect sensor to measure the pH of the contents of the growth chamber.

41. The device of claim 1, comprising an optical sensor.

42. The device of claim 1, wherein the valve system meters fluid into the reservoir according to an actuation sequence of opening and closing the valve.

43. The device of claim 42, wherein the metered amount of fluid may be predetermined.

44. The device of claim 43, wherein the metered fluid injector injects between approximately 1 and 500 nL of fluid into the reservoir.

45. The device of claim 42, wherein the valve system comprises three valves.

46. The device of claim 43, wherein the actuation sequence is 100, 101, 001, 011, 111, and wherein '1' indicates a closed valve and '0' indicates an open valve.

47. The device of claim 1, wherein the valve system meters fluid for more than one bioreactor.

48. The device of claim 1, comprising an inoculum preparation chamber, wherein the inoculum preparation chamber is filled with a starter culture and allows the culture to grow before being delivered to the growth chamber.

49. The device of claim 1, comprising at least one gas switch in communication with the mixer, wherein the gas switch controls the oxygenation concentration in the mixer.

50. The device of claim 49, comprising at least one gas inlet to provide gas to the mixer, and at least one gas outlet to release gas from the mixer.

51. The device of claim 49, comprising a source of oxygen enriched air.

52. The device of claim 49, comprising a source of oxygen neutral air.

53. The device of claim 49, comprising a source of oxygen deficient air.

54. The device of claim 49, wherein the at least one gas switch comprises a solenoid switch.

55. The device of claim 1, wherein the at least one sensor senses pH.

56. The device of claim 1, wherein the growth chamber has an internal volume of less than approximately 1 mL.

57. The device of claim 1, wherein one spatial dimension of the growth chamber is at least approximately 10 times smaller than the other two spatial dimensions of the growth chamber.

* * * * *